United States Patent [19]
Cunningham et al.

[11] Patent Number: 6,087,062
[45] Date of Patent: Jul. 11, 2000

[54] POLYBORATE COINITIATORS FOR PHOTOPOLYMERIZATION

[75] Inventors: Allan Francis Cunningham, Marly, Switzerland; Martin Kunz, Efringen-Kirchen, Germany

[73] Assignee: Ciba Specialty Chemicals Corporation, Tarrytown, N.Y.

[21] Appl. No.: 09/081,430

[22] Filed: May 19, 1998

[30] Foreign Application Priority Data

May 23, 1997 [CH] Switzerland .................... 1205/97

[51] Int. Cl.$^7$ .................... G03C 1/73; C08F 2/46; C08F 4/52; C07F 5/02
[52] U.S. Cl. .................... 430/270.1; 522/7; 522/25; 522/29; 526/196; 568/3; 568/6
[58] Field of Search .................... 558/286; 562/7; 549/213; 568/3, 6; 564/9; 522/6, 12, 25, 26, 27, 28, 29, 43, 46, 7; 430/281.1, 270.1; 526/196

[56] References Cited

U.S. PATENT DOCUMENTS

| | | | |
|---|---|---|---|
| 2,872,479 | 2/1959 | Letsinger et al. | 260/500 |
| 3,163,679 | 12/1964 | Koster et al. | 260/606.5 |
| 3,311,662 | 3/1967 | Washburn et al. | 260/606.5 |
| 4,772,530 | 9/1988 | Gottschalk et al. | 430/138 |
| 4,772,541 | 9/1988 | Gottschalk et al. | 430/339 |
| 4,954,414 | 9/1990 | Adair et al. | 430/138 |
| 5,055,372 | 10/1991 | Shanklin et al. | 430/138 |
| 5,151,520 | 9/1992 | Gottschalk et al. | 548/110 |
| 5,807,905 | 9/1998 | Cunningham et al. | 522/25 |

FOREIGN PATENT DOCUMENTS

| | | | |
|---|---|---|---|
| 0710663 | 5/1996 | European Pat. Off. | |
| 0775706 | 5/1997 | European Pat. Off. | |
| 0811627 | 12/1997 | European Pat. Off. | C07F 5/02 |

OTHER PUBLICATIONS

Zeitschrift für Chemie, (1966) pp. 34–35.
Zeitschrift für Chemie, (1966) pp. 435–436.
Derwent Abst. 97–283080/26 for EP 0775706–A2.
Chem Abstr. 128:61925.

*Primary Examiner*—Janet Baxter
*Assistant Examiner*—Rosemary Ashton
*Attorney, Agent, or Firm*—Luther A. Hall

[57] ABSTRACT

Compounds of the formula I and II

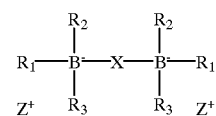

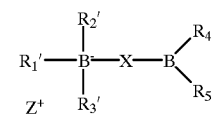

in which $R_1$, $R_2$ and $R_3$ are, for example, unsubstituted or substituted phenyl, where none of the radicals $R_1$–$R_3$ is a phenyl radical which is substituted ortho to the bond to the borate atom;

$R_1'$, $R_2'$, $R_3'$ have one of the meanings of $R_1$–$R_3$;

$R_4$ and $R_5$ are OH or $OR_6$ or have one of the meanings of $R_1$–$R_3$ and the radicals $R_1'$, $R_2'$, $R_3'$, $R_4$ and $R_5$ can also be substituted ortho to the bond to the borate atom;

$R_6$ is, for example, unsubstituted or $C_1$–$C_{12}$alkoxy- or halo-substituted $C_1$–$C_{12}$alkyl;

X is, for example, $C_1$–$C_{20}$alkylene which is unsubstituted or substituted or which is interrupted by one or more aromatic hydrocarbons, or X is, for example, $C_3$–$C_{12}$cycloalkylene or polycycloalkylene; and $Z^+$ is a radical which is able to form positive ions;

are suitable as coinitiators for the photopolymerization of ethylenically unsaturated compounds.

26 Claims, No Drawings

POLYBORATE COINITIATORS FOR PHOTOPOLYMERIZATION

The invention relates to mono- and polyborate compounds derived from polyboranes, to their use as photoinitiators in combination with electron acceptors, and to photopolymerizable compositions comprising the photoinitiators of the invention.

Monoborate compounds in association with ionic dyes have been described in the prior art as photoinitiators. For example, U.S. Pat. Nos. 4,772,530, 4,772,541 and 5,151,520 describe monocyclic triarylalkylborate anions with cationic dyes, such as cyanines, rhodamines, etc., as counterions. These compounds are employed as photoinitiators. In U.S. Pat. No. 4,954,414, cationic transition metal complexes are used together with triarylalkylborate anions in photopolymerizable compositions. From U.S. Pat. No. 5,055,372 it is also known to use quaternary ammonium compounds, for example tetramethylammonium, pyridinium, cetylpyridinium etc., as cationic counterions to the triarylalkylborate. In that publication the borates are employed in association with aromatic ketone initiator compounds in photocurable materials. In Z. Chem. 6 (1966), 34, H. Holzapfel, P. Nenning and O. Wildner describe the preparation of the sodium phenylborate of 1,4-bis(diphenylboryl)benzene. In Z. Chem. 6 (1966), 435 H. Holzapfel, P. Nenning and H. Stirn disclosed the preparation of the corresponding bisphenylborates and the corresponding naphthyl-substituted compounds. U.S. Pat. No. 3,311,662 describes polyborates which are employed as fungicides and bactericides. None of these documents discloses polyborate compounds as photoinitiators. In EP 775 706, polyborate compounds are disclosed as photoinitiators.

For the extensive range of applications for photoinitiators, there is a need in industry for reactive compounds.

It has now surprisingly been found that certain novel polyborate compounds are suitable as coinitiators in combination with electron acceptor compounds as initiators for the photopolymerization of ethylenically unsaturated compounds. Here, the electron acceptor compound may already be present as an ionic constituent in the borate compounds of the invention.

The invention provides compounds of the formula I and II

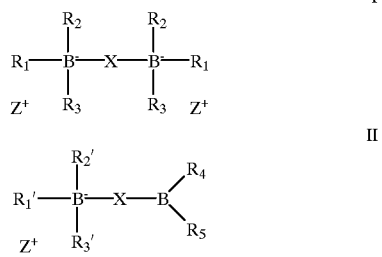

in which

R$_1$, R$_2$ and R$_3$ independently of one another are phenyl or another aromatic radical, which radicals are unsubstituted or substituted by C$_1$–C$_6$alkyl, halo-, OR$_6$- and/or NR$_8$R$_9$-substituted C$_1$–C$_6$alkyl, OR$_6$, S(O)$_p$R$_7$, OS(O)$_2$R$_7$, NR$_8$R$_9$, S(O)$_p$NR$_8$R$_9$, C(O)NR$_8$R$_9$, SiR$_{11}$R$_{12}$R$_{13}$, P(O)$_q$R$_{14}$R$_{15}$, halo or

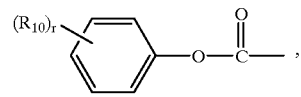

and none of the radicals R$_1$–R$_3$ is a phenyl radical substituted ortho to the bond to the borate atom or another aromatic radical substituted ortho to the borate atom;

p is 0, 1 or 2;

q is 0 or 1;

r is a number from 0 to 5;

R$_1$', R$_2$' and R$_3$' have one of the meanings of R$_1$–R$_3$, where the radicals R$_1$', R$_2$' and R$_3$' can also be substituted ortho to the bond to the borate atom;

R$_4$ and R$_5$ are OH or OR$_6$ or have one of the meanings of R$_1$–R$_3$, where the radicals R$_4$ and R$_5$ can also be substituted ortho to the bond to the borate atom;

R$_6$ and R$_7$ independently of one another are C$_3$–C$_{12}$cycloalkyl, C$_2$–C$_8$alkenyl, C$_1$–C$_{12}$alkyl, C$_1$–C$_{12}$alkoxy- or halo-substituted C$_1$–C$_{12}$alkyl, phenyl, mono- to penta-C$_1$–C$_6$alkyl-, -C$_1$–C$_{12}$alkoxy- or -halo-substituted phenyl or phenyl-C$_1$–C$_6$alkyl, mono- to penta-C$_1$–C$_6$alkyl-, -C$_1$–C$_{12}$alkoxy- or -halo-substituted phenyl-C$_1$–C$_6$alkyl;

R$_8$, R$_9$, R$_{11}$, R$_{12}$, R$_{13}$, R$_{14}$ and R$_{15}$ independently of one another have one of the meanings of R$_6$, or R$_8$ and R$_9$, together with the nitrogen atom to which they are attached, form a 5- or 6-membered ring which may additionally contain oxygen or sulfur atoms;

R$_{10}$ is hydrogen or C$_1$–C$_{12}$alkyl;

X is C$_1$–C$_{20}$alkylene, which is unsubstituted or substituted by OR$_6$', S(O)$_p$R$_7$', OS(O)$_2$R$_7$', NR$_8$'R$_9$', C(O)NR$_8$'R$_9$', SiR$_{11}$'R$_{12}$'R$_{13}$', P(O)$_q$R$_{14}$'R$_{15}$', halo, (BR$_1$R$_2$R$_3$)$^-$Z$^+$, BR$_4$R$_5$, phenyl or

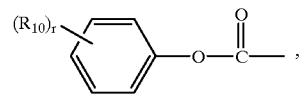

where the phenyl radical is unsubstituted or substituted 1 to 5 times by halo, or by C$_1$–C$_{12}$alkyl, or (BR$_1$R$_2$R$_3$)$^-$Z$^+$- or BR$_4$R$_5$-substituted C$_1$–C$_{12}$alkyl, or by C$_1$–C$_{12}$dialkylamino, (BR$_1$R$_2$R$_3$)$^-$Z$^+$- or BR$_4$R$_5$-substituted C$_1$–C$_{12}$dialkylamino, or by C$_1$–C$_{12}$alkoxy, (BR$_1$R$_2$R$_3$)$^-$Z$^+$- or BR$_4$R$_5$-substituted C$_1$–C$_{12}$alkoxy, or X is C$_2$–C$_{20}$alkylene which is interrupted by one or more groups -O-, -S(O)$_p$-, -NR$_{16}$-, -OSiR$_{17}$R$_{18}$O-, -SiR$_{17}$R$_{18}$-, or X is C$_2$–C$_{20}$alkylene which is interrupted by one or more aromatic radicals, where the aromatic radicals are unsubstituted or substituted 1 to 5 times by halo, (BR$_1$R$_2$R$_3$)$^-$Z$^+$- or BR$_4$R$_5$, C$_1$–C$_6$alkyl, (BR$_1$R$_2$R$_3$)$^-$Z+-or BR$_4$R$_5$-substituted C$_1$–C$_6$alkyl, or by C$_1$–C$_{12}$alkoxy, (BR$_1$R$_2$R$_3$)$^-$Z$^+$- or BR$_4$R$_5$-substituted C$_1$–C$_{12}$alkoxy or by C$_1$–C$_{12}$dialkylamino, (BR$_1$R$_2$R$_3$)$^-$Z$^+$- or BR$_4$R$_5$-substituted C$_1$–C$_{12}$dialkylamino;

or X is C$_3$–C$_{12}$cycloalkylene or C$_2$–C$_8$alkenylene, which radicals are unsubstituted or substituted by OR$_6$', S(O)$_p$R$_7$', OS(O)$_2$R$_7$', NR$_8$'R$_9$', C(O)NR$_8$'R$_9$', SiR$_{11}$'R$_{12}$'R$_{13}$', P(O)$_q$R$_{14}$'R$_{15}$', halo, C$_1$–C$_{12}$alkyl, (BR$_1$R$_2$R$_3$)$^-$Z$^+$, BR$_4$R$_5$ or phenyl or

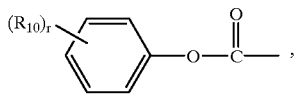

where the phenyl radical is $C_1$–$C_{12}$alkyl, substituted 1 to 5 times by halo, unsubstituted or $(BR_1R_2R_3)^-Z^+$- or $BR_4R_5$-substituted $C_1$–$C_{12}$alkyl, or by $C_1$–$C_{12}$dialkylamino, $(BR_1R_2R_3)^-Z^+$- or $BR_4R_5$-substituted $C_1$–$C_{12}$dialkylamino, or by $C_1$–$C_{12}$alkoxy, $(BR_1R_2R_3)^-Z^+$- or $BR_4R_5$-substituted $C_1$–$C_{12}$alkoxy;

or X is $C_3$–$C_{12}$cycloalkytene or $C_2$–$C_8$alkenylene which is interrupted by one or more groups -O-, -S(O)$_p$-, -NR$_{16}$-, -OSiR$_{17}$R$_{18}$O-, -SiR$_{17}$R$_{18}$-;

or X is a radical of the formula X–XVII

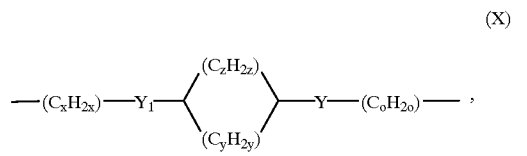 (X)

 (XI)

 (XII)

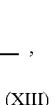 (XIII)

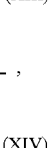 (XIV)

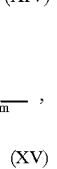 (XV)

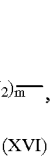 (XVI)

 (XVII)

or X is polycycloalkylene;

x, y, z and o independently of one another are a number from 0 to 8, where the cycloalkyl rings in the formulae (X) and (XIII) in each case contain not more than 12 carbon atoms;

m is a number from 1 to 6;

$R_6'$ and $R_7'$ independently of one another are $C_1$–$C_{12}$alkyl, which is unsubstituted or substituted by $C_1$–$C_{12}$alkoxy, $(BR_1R_2R_3)^-Z^+$- or $BR_4R_5$-substituted $C_1$–$C_{12}$alkoxy, or $C_1$–$C_{12}$dialkylamino, $(BR_1R_2R_3)^-Z^+$- or $BR_4R_5$-substituted $C_1$–$C_{12}$dialkylamino, or by halo, $(BR_1R_2R_3)^-Z^+$ or $BR_4R_5$, or $R_6'$ and $R_7'$ are $C_3$–$C_{12}$cycloalkyl or $C_1$–$C_{12}$alkoxy-, $C_1$–$C_{12}$-dialkylamino-, halo-, $(BR_1R_2R_3)^-Z^+$- or $BR_4R_5$-substituted $C_3$–$C_{12}$cycloalkyl, or $R_6'$ and $R_7'$ are phenyl or mono- to penta-halo-substituted phenyl, or $R_6'$ and $R_7'$ are phenyl, which is substituted by $C_1$–$C_6$alkyl, or $(BR_1R_2R_3)^-Z^+$- or $BR_4R_5$-substituted $C_1$–$C_6$alkyl, $C_1$–$C_{12}$alkoxy, $(BR_1R_2R_3)^-Z^+$- or $BR_4R_5$-substituted $C_1$–$C_{12}$alkoxy, $C_1$–$C_{12}$dialkylamino, $(BR_1R_2R_3)^-Z^+$- or $BR_4R_5$-substituted $C_1$–$C_{12}$dialklamino, or $R_6'$ and $R_7'$ are phenyl-$C_1$–$C_6$alkyl or mono- to penta-halo-substituted phenyl-$C_1$–$C_6$alkyl, or $R_6'$ and $R_7'$ are phenyl-$C_1$–$C_6$alkyl which is substituted by $C_1$–$C_6$alkyl, $(BR_1R_2R_3)^-Z^+$- or $BR_4R_5$-substituted $C_1$–$C_6$alkyl or $C_1$–$C_{12}$alkoxy, $(BR_1R_2R_3)^-Z^+$- or $BR_4R_5$-substituted $C_1$–$C_{12}$-alkoxy or $C_1$–$C_{12}$dialkylamino, $(BR_1R_2R_3)^-Z^+$- or $BR_4R_5$-substituted $C_1$–$C_{12}$-dialkylamino;

$R_8'$, $R_9'$, $R_{11}'$, $R_{12}'$, $R_{13}'$, $R_{14}'$ and $R_{15}'$ independently of one another have one of the meanings of $R_6'$, or $R_8'$ and $R_9'$, together with the nitrogen atom to which they are attached, form a 5- or 6-membered ring which may additionally contain oxygen or sulfur atoms;

$R_{16}$ is hydrogen or has one of the meanings of $R_6'$;

$R_{17}$ and $R_{18}$ have one of the meanings of $R_6'$;

Y, $Y_1$ and $Y_2$ independently of one another are a direct bond, O, S, $SO_2$, $NR_{16}$, $SiR_{17}R_{18}$ or -$CR_{19}R_{20}$-;

$R_{19}$ and $R_{20}$ independently of one another are hydrogen or $C_1$–$C_{12}$alkyl; and $Z^+$ is a radical which is able to form positive ions.

Aromatic hydrocarbons as may be present in the compounds of the invention may, for example, contain one or more, especially one or two, heteroatoms. Examples of suitable heteroatoms are N, P, O or S, preferably N or O. Examples of aromatic hydrocarbon radicals are phenyl, α- and β-naphthyl, stilbenyl, biphenyl, o-, m-, p-terphenyl, triphenylphenyl, binaphthyl, anthracyl, phenanthryl, pyrenyl, furan-2-yl or furan-3-yl, thiophen-2-yl or thiophen-3-yl, pyridin-2-yl, or pyridin-3-yl, quinolyl or isoquinolyl.

Also suitable are aromatic hydrocarbon radicals of the formula

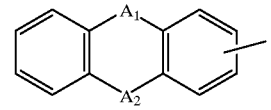

in which $A_1$ and $A_2$ independently of one another are a single bond, -$(CH_2)_u$-, -CH=CH-, -C(O)-, -$NR_{16}$-, $S(O)_p$,

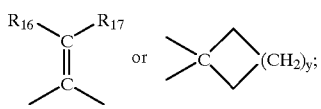
$R_{17}$, $R_{16}$ and p are as defined above, u is a number 1, 2 or 3, v is 2 or 3. Examples of such radicals are anthracyl, fluorenyl, thianthryl, xanthyl, acridinyl, phenazinyl, phenothiazinyi, phenoxathiinyl, phenoxazinyl.
Stilbenyl is
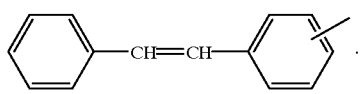
Biphenyl is
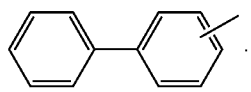
o-, m- or p-terphenyl are
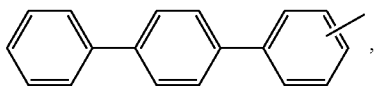
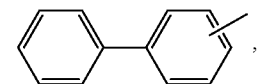
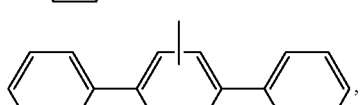
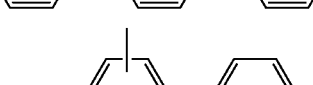
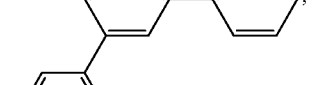
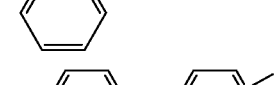
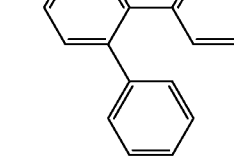
-continued
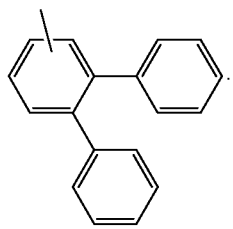
Triphenylphenyl is
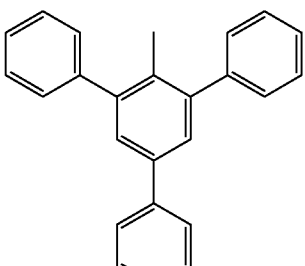
or
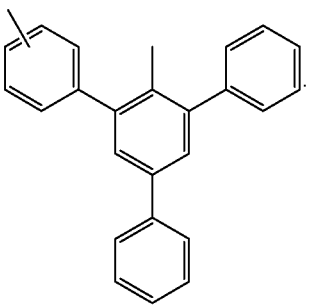
Binaphthyl is
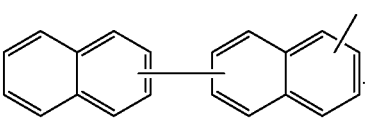
Anthracyl is
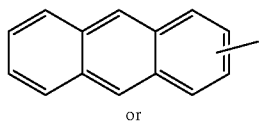
or
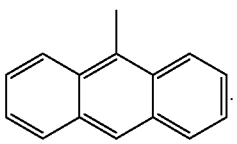

Phenanthryl is

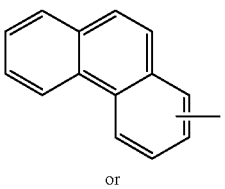

or

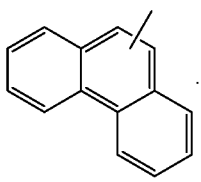

Pyrenyl is

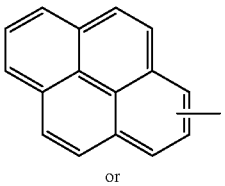

or

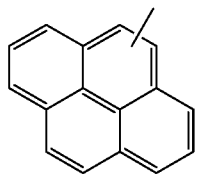

Furanyl is furan-2-yl or furan-3-yl. Thiophenyl is thiophen-2-yl or thiophen-3-yl. Pyridinyl is pyridin-2-yl, pyridin-3-yl or pyridin-4-yl. Quinolinyl is

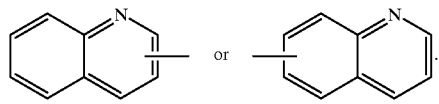

Isoquinolinyl is

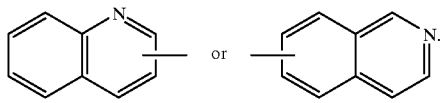

Substituted radicals phenyl, stilbenyl, biphenyl, o-, m- or p-terphenyl, triphenylphenyl, naphthyl, binaphthyl, anthracyl, phenanthryl, pyrenyl, ferrocenyl, furanyl, thiophenyl, pyridinyl, quinolinyl or isoquinolinyl are substituted 1 to 4 times, for example 1, 2 or 3 times, especially 2 or 3 times.

$C_1$–$C_{12}$alkyl is linear or branched and is, for example, $C_1$–$C_8$-, $C_1$–$C_6$- or $C_1$–$C_4$alkyl. Examples are methyl, ethyl, propyl, isopropyl, n-butyl, sec-butyl, iso-butyl, tert-butyl, pentyl, hexyl, heptyl, 2,4,4-trimethylpentyl, 2-ethylhexyl, octyl, nonyl, decyl or dodecyl. They are exemplified by $C_1$–$C_8$alkyl, especially $C_1$–$C_6$alkyl, preferably $C_1$–$C_4$alkyl.

$C_3$–$C_{12}$cycloalkyl is for example cyclopropyl, cyclopentyl, cyclohexyl, cyclooctyl, cyclododecyl, especially cyclopentyl, cyclohexyl and cyclododecyl, preferably cyclohexyl, cyclooctyl and cyclododecyl, in particular cyclohexyl and cyclooctyl.

$C_1$–$C_{12}$alkoxy is linear or branched and is for example $C_1$–$C_8$-, $C_1$–$C_6$- or $C_1$–$C_4$alkoxy. Examples are methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, iso-butyloxy, tert-butyloxy, preferably methoxy.

Halo is fluoro, chloro, bromo and iodo, especially fluoro, chloro and bromo, preferably chloro and fluoro.

If $C_1$–$C_{12}$alkyl is substituted one or more times by halo, then there are for example 1 to 3 or 1 or 2 halo substitutents on the alkyl radical. Preference is given to $CCl_3$ and $CF_3$, especially $CF_3$.

Phenyl-$C_1$–$C_6$alkyl is for example benzyl, phenylethyl, α-methylbenzyl, phenylpentyl, phenylhexyl or α,α-dimethylbenzyl, especially benzyl. Substituted phenyl-$C_1$–$C_6$alkyl is substituted one to four times, for example once, twice or three times, especially twice or three times, on the phenyl ring.

$C_1$–$C_{12}$dialkylamino is a dialkylamino radical which can contain a total of up to 12 carbon atoms. The two alkyl radicals on the nitrogen atom may contain a different number of carbon atoms. Examples are dimethylamino, diethylamino, ethylmethylamino, dipropylamino, dipentylamino, dibutylamino, dihexylamino, ethyidecylamino, preferably dimethylamino.

Where $R_8$ and $R_9$ or $R_8'$ and $R_9'$, together with the nitrogen atom to which they are attached, form a 5- or 6-membered ring which may additionally contain oxygen or sulfur atoms, this ring can be saturated or unsaturated. Examples are morpholine, piperidine, thiazoline, oxazole, oxazine rings, especially morpholine rings.

X as $C_1$–$C_{20}$alkylene is linear or branched alkylene such as methylene, ethylene, propylene, 1-methylethylene, 1,1-dimethylethylene, butylene, 1-methylpropylene, 2-methylpropylene, pentylene, hexylene, heptylene, octylene, nonylene, decylene, dodecylene, tetradecylene, hexadecylene or octadecylene. In particular, X is $C_1$–$C_{12}$alkylene, e.g. ethylene, decylene,

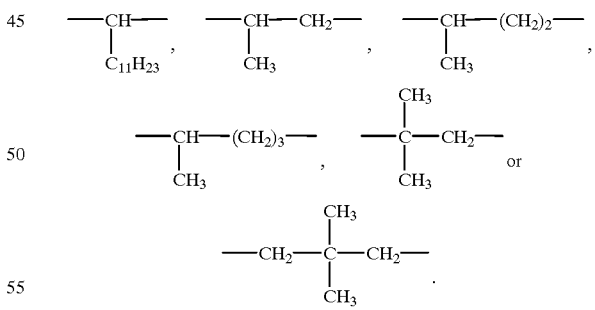

The alkylene radicals $C_xH_{2x}$, $C_yH_{2y}$, $C_zH_{2z}$ and $C_oH_{2o}$ are also linear or branched.

X as $C_2$–$C_{20}$alkylene which is interrupted one or more times by -O-, -S(O)$_p$- or -NR$_{16}$- is, for example, interrupted 1–9 times, e.g. 1–7, 1–5, 1–3 or 1 or 2 times by -O-, -S(O)$_p$- or -NR$_{16}$-. This produces structural units such as, for example, -CH$_2$—O—CH$_2$-, -CH$_2$—S—CH$_2$-, -CH$_2$—N(CH$_3$)—CH$_2$-, -CH$_2$CH$_2$—O—CH$_2$CH$_2$-, -[CH$_2$CH$_2$O]$_y$-, -[CH$_2$CH$_2$O]$_y$—CH$_2$-, where y=1–9, -(CH$_2$CH$_2$O)$_7$CH$_2$CH$_2$-, -CH$_2$—CH(CH$_3$)—O—CH$_2$—CH(CH$_3$)- or -CH$_2$—CH(CH$_3$)—O—CH$_2$—CH$_2$CH$_2$-. -OR$_6$- or -OR$_6$'-substituted C$_1$–C$_{20}$alkylene is, for example,

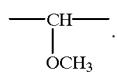

Preference is given to sequences of ethylene oxide units.

Where X is C$_1$–C$_{20}$alkylene which is interrupted by one or more aromatic hydrocarbons or other heterocycles where the aromatic hydrocarbons are unsubstituted or substituted 1 to 5 times by halo, (BR$_1$R$_2$R$_3$)$^{31}$ Z$^+$ or BR$_4$R$_5$, unsubstituted or (BR$_1$R$_2$R$_3$)$^-$Z$^+$- or BR$_4$R$_5$-substituted C$_1$–C$_6$alkyl, or by unsubstituted or (BR$_1$R$_2$R$_3$)$^-$Z$^+$- or BR$_4$R$_5$-substituted C$_1$–C$_{12}$alkoxy or by unsubstituted or (BR$_1$R$_2$R$_3$)$^-$Z$^+$- or BR$_4$R$_5$-substituted C$_1$–C$_{12}$dialkylamino, then this means, for example, that X is an alkylene of the following formulae III–IX:

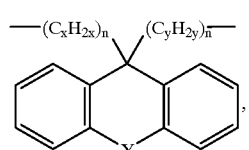 (III)

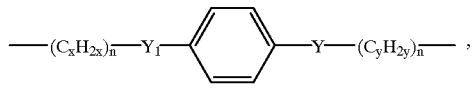 (IV)

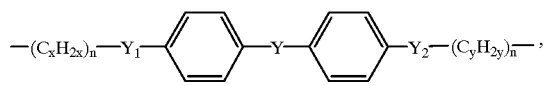 (V)

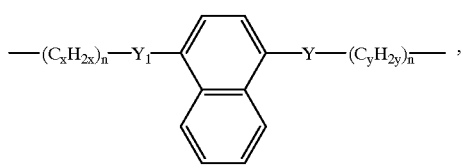 (VI)

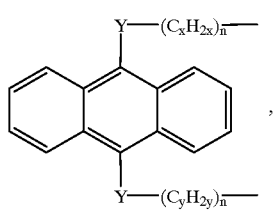 (VII)

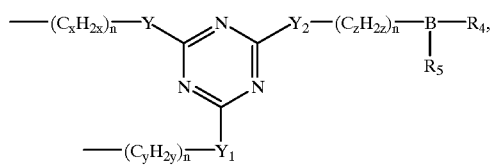 (VIII)

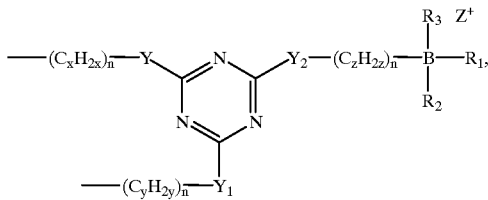 (IX)

in which n is a number from 1 to 6 and x, y, z, R$_1$, R$_2$, R$_3$, R$_4$, R$_5$, Y, Y$_1$, Y$_2$ and Z are as defined above and the phenyl rings may carry the substituents indicated. Preference is given to formula IV, where Y and Y$_1$=CH$_2$ or -O-. Preferred substituents for the phenyl rings are C$_1$–C$_{12}$alkoxy and (BR$_1$R$_2$R$_3$)$^-$Z$^+$.

C$_3$–C$_{12}$cycloalkylene is, for example, C$_3$–C$_{10}$-, C$_5$–C$_{12}$-, C$_5$–C$_{10}$-, C$_6$–C$_{12}$- or C$_6$–C$_8$cycloalkylene and is, for example, cyclopropylene, cyclopentylene, cyclohexylene, cyclooctylene, cyclododecylene, especially cyclopentylene, cyclooctylene and cyclohexylene, preferably cyclohexylene and cyclooctylene.

C$_3$–C$_{12}$cycloalkylene is also, however, for example, structural units

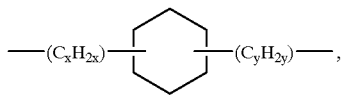

where x and y independently of one another are 0–6 and the sum of x+y≦6, or

where x and y independently of one another are 0–7 and the sum of x+y≦7. Also embraced by the term C$_3$–C$_{12}$cycloalkylene are, for example, bicyclic cycloalkylenes, such as the following structures, for example:

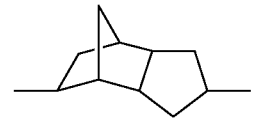

or else $C_1$–$C_{12}$alkyl-substituted cycloalkylene, such as

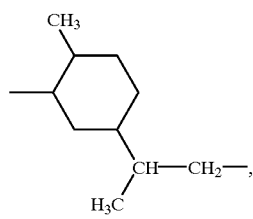

for example.

The term polycycloalkylene denotes the sequential arrangement of identical or different cycloalkylene rings having up to 50 carbon atoms, e.g.:

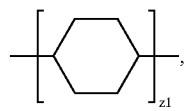

where z1 is a number from 2 to 8.

$C_2$–$C_8$alkenylene can be mono- or polyunsaturated and can be linear or branched radicals and is, for example, ethenylene, 1-propenylene, 1-butenylene, 3-butenylene, 2-butenylene, 1,3-pentadienylene, 5-hexenylene or 7-octenylene.

Depending on which radicals are employed as X it is possible for isomeric compounds to be formed. The invention provides all of the isomers. Photoinitiator effectiveness is generally independent of the particular isomeric form.

Radicals suitable as a counterion $Z^+$ to the negative borate in the formula I are in general those which are able to form positive ions.

Examples of these are alkali metals, especially lithium or sodium, quaternary ammonium compounds, especially ammonium or tetraalkylammonium, dye cations or cationic transition metal coordination complex compounds.

Examples of tetraalkylammonium are, in particular, tetramethylammonium or tetra-butylammonium, although tris-alkylammonium ions, e.g. trimethylammonium, are also suitable. Suitable phosphonium and ammonium counterions are those of the formulae $^+PR_wR_xR_yR_z$ and $^+NR_wR_xR_yR_z$, where $R_w$, $R_x$, $R_y$, and $R_z$ independently of one another are hydrogen, unsubstituted or substituted alky, cycloalkyl, alkenyl, phenyl or phenylalkyl. Substituents for these alkyl, cycloalkyl, alkenyl, phenyl or phenylalkyl radicals are, for example, halide, hydroxyl, heterocycloalkyl (e.g. epoxy, aziridyl, oxetanyl, furanyl, pyrrolidinyl, pyrrolyl, thiophenyl, tetrahydrofuranyl, etc.), dialkylamino, amino, carboxyl, alkyl- and arylcarbonyl and aryloxy- and alkoxycarbonyl.

The tetravalent nitrogen may also be part of a 5- or 6-membered ring, in which case this ring may in turn be fused to other ring systems. These systems may also contain additional heteroatoms, such as S, N, O.

The tetravalent nitrogen may also be part of a polycyclic ring system, for example azoniapropellane. These systems may also contain further heteroatoms, such as S, N, O.

Also suitable as the counterions $Z^+$ are polyammonium salts and polyphosphonium salts, especially the bis salts, in which it is possible for the same substituents to be present as described above for the "mono" compounds.

The ammonium salts and phopshonium salts may also be substituted by neutral dyes (e.g. thioxanthenes, thioxanthones, coumarins, ketocoumarins, etc.). Such salts are obtained by the reaction of the ammonium salts and phosphonium salts, substituted by reactive groups (e.g. epoxy, amino, hydroxy, etc.), with appropriate derivatives of neutral dyes. Corresponding examples are described in EP 224967 (QUANTACURE QTX).

Similarly, the ammonium salts and phosphonium salts which are suitable as the counterions $Z^+$ can also be substituted by colourless electron acceptors (e.g. benzophenones): Examples of these are (from International Bio-Synthetics)

QUANTACURE ABQ

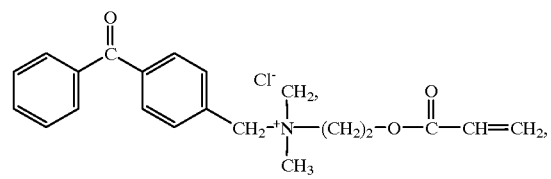

QUANTACURE BPQ

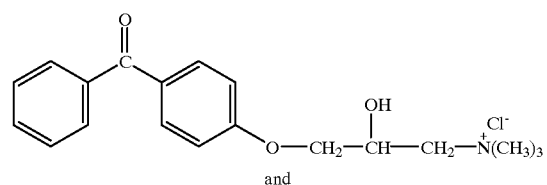

and

QUANTACURE BTC

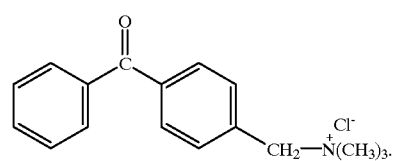

Other suitable quaternary ammonium compounds are, for example, trimethylcetylammonium or cetylpyridinium.

Other examples of ions to be used as positive counterions $Z^+$ in the compound of the formula I include the following:

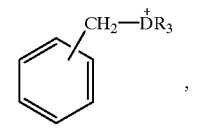

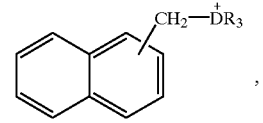

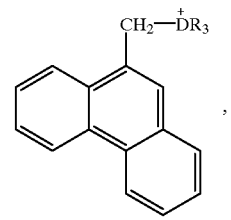

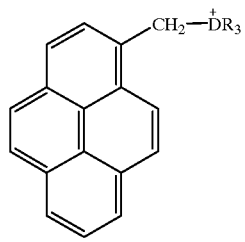

in which D is P, N or S and R is an alkyl or aryl radical. Also suitable are compounds such as

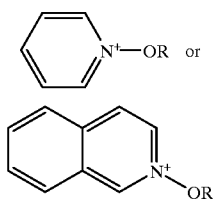

(described by Yagci et al. in J. Polym. Sci. Part A: Polymer Chem. 1992, 30, 1987 and Polymer 1993, 34(6), 1130), or compounds such as

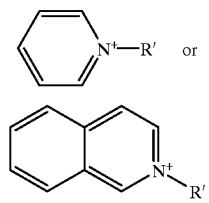

where R'=unsubstituted or substituted benzyl or phenacyl (described in JP-A Hei 7 70221). In these compounds, the aromatic rings in the pyridinium may also be substituted.

Other ions which can be employed as positive counterions $Z^+$ to the borate are onium ions, for example iodonium or sulfonium ions. Examples of such counterions to the borate are radicals of the formula

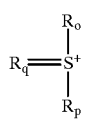

as described, for example in EP 555058 and EP 690074.

Also of interest as counterions are

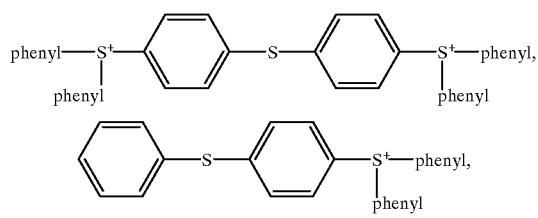

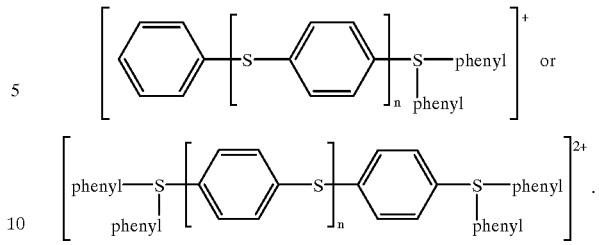

Other suitable counterions for the borates of the invention are cations of the formula

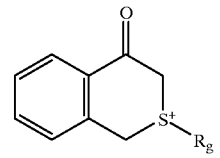

in which $R_g$ is an alkyl radical, especially ethyl, or is benzyl and where the aromatic ring can carry further substituents. Further suitable counterions are halonium ions, especially diaryliodonium ions, as described for example in EP 334056 and EP 562897.

However, cations of ferrocenium salts are also suitable, as described in EP 94915 and EP 109851, for example

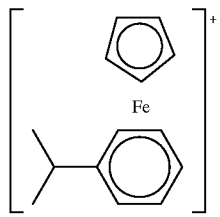

Other suitable "onium" cations, such as ammonium, phosphonium, sulfonium, iodonium, selonium, arsonium, tellonium, bismuthonium, are described, for example in Japanese Patent Application Hei 6 266 102.

Examples of cationic transition metal complex compounds which are suitable as counterion are described in U.S. Pat. No. 4,954,414. Of particular interest are bis(2,2'-bipyridine)(4,4'-dimethyl- 2,2'-bipyridine)ruthenium, tris(4, 4'-dimethyl-2,2'-bipyridine)ruthenium, tris(4,4'-dimethyl-2, 2'-bipyridine)iron, tris(2,2',2"-terpyridineruthenium, tris(2, 2'-bipyridine)ruthenium and bis(2,2'-bipyridine)(5-chloro-1, 10-phenanthroline)ruthenium.

Examples of suitable dyes are cations of triarylmethanes, for example Malachite Green, indolines, thiazines, for example Methylene Blue, xanthones, thioxanthones, oxazines, acridines, cyanines, rhodamines, phenazines, for example safranin, preferably cyanines and thioxanthones.

It is also possible to use divalent dyes, in other words for example those having two positive charges, in which case then two borate units of the formula I or II of the invention, or else a combination of a borate of the formula I or II of the invention with another known borate, are used as anions. Examples of divalent cationic dyes are given in JP Kokai Hei 4-146 905.

Some of the compounds of the invention exhibit good stability to acid and can therefore also be employed in acidic formulation, and also, for example, in combination with dyes containing acid groups.

The borates of the formula I and II of the invention are prepared, for example, by 1. addition of one or, respectively, 2 equivalents of an organometallic reagent onto a corresponding borane (Ia, IIa) and 2. optional subsequent cation exchange reaction.

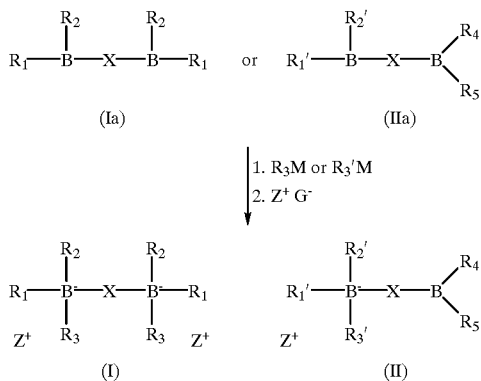

The definitions of the radicals $R_1$–$R_5$, $R_1'$–$R_3'$, X and Z are as indicated above. M is a metal atom, for example Li, Mg etc., and G is an anion.

The reaction conditions for working with organometallic reagents are generally familiar to the skilled worker. Thus the reaction is judiciously carried out in an inert organic solvent, for example an ether or aliphatic hydrocarbon, such as diethyl ether, tetrahydrofuran or hexane. Suitable organometallic reagents for preparing the bisborates of the invention are, for example, the lithium compounds of the corresponding aliphatic and aromatic hydrocarbon radicals. It is likewise possible, for example, to use Grignard reagents, zinc or sodium. The reaction with the organometallic reagent is judiciously carried out with exclusion of air in an inert gas atmosphere, for example under nitrogen. The reaction is generally performed with cooling to 0° C. or below followed by heating to room temperature.

It is judicious to stir the reaction mixture. The products are isolated and purified by methods likewise generally known to the skilled worker, such as chromatography, recrystallization, etc., for example. Thus, for example, impurities are judiciously removed by washing the product with a boiling solvent, followed by filtration.

It is also possible to obtain the borates directly from solution during the preparation of the polyborane precursors, without isolating them beforehand.

The preparation of the compounds of the invention generally gives rise to isomer mixtures. These can be resolved by methods which are customary in the art and known to the skilled worker, or else can be employed as initiator directly, in the form of the isomer mixture.

Where the compounds of the formula I or II of the invention comprise a dye radical as the cation, these compounds are prepared by cation exchange reaction of a corresponding borate salt with a dye. Examples of borate salts suitable for the exchange are the sodium, lithium, magnesium, ammonium or tetraalkylammonium salts.

Another preparation method for compounds of the formula I or II starts from poly(dialkoxyboryl), poly(diaryloxyboryl) or poly(dihaloboryl) compounds as intermediates. This reaction is depicted in the equation below:

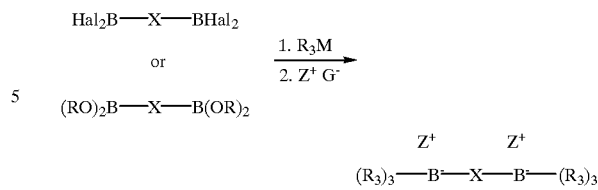

The definitions of the radicals $R_3$, X, Z and G are as indicated above. Hal is halo, R an organic radical.

A third variant of preparing the borates of the invention is the addition reaction of dimetallated compounds with triarylboranes (Negishi et al *J. Org. Chem.* 1990, 55, 5406). Although dilithiated reagents are employed by way of example in the equation, it is possible to employ a wide range of dimetallated compounds in this reaction.

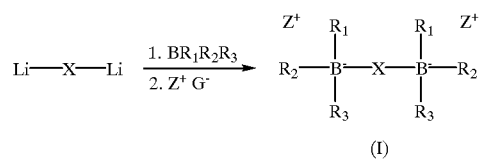

The definitions of the radicals $R_1$, $R_2$, $R_3$, X, Z and G are as indicated above.

The borates of the invention having the general structure II are formed if, for example, a mixed primary/secondary poly(dialkoxy-, diaryloxy- or dihaloboryl) compound is reacted with an ortho-substituted aryl-Grignard reagent. The presence of the α-alkyl group prevents the introduction of the third aryl radical, and so the monoborate is formed.

These monoborates comprise oxygen-sensitive borane units, which can be hydrolysed and/or oxidized to give the boric acids or boric esters, respectively, of formula II where $R_4$ and/or $R_5$=OH or $OR_6$.

The diarylhaloboranes or diarylalkoxyboranes used as starting materials can be obtained, for example, by the procedures of Haubold et al (*J. OrganomeL Chem.* 1986, 315, 1), Nöth et al. (*J. Organomet. Chem.* 1968, 11, 399), Köster et al. (*Inorg. Synth.* 19, 14, 152) and Cole et al. (*Organometallics* 1992, 11, 652) or by methods described in *Boranes in Organic Chemistry;* Cornell University Press, Ithaca, N.Y., 1972; A. Pelter, K. Smith and H. C. Brown, *Borane Reagents;* Academic Press, London, 1988). Reduction gives the diarylboranes (Jacob *J. Organomet. Chem.* 1978, 156, 101; Pelter et al. *J. C. S. Chem. Commun.* 1975, 532; Maddocks et al. *J. C. S. Perkin Trans.* 1 1981, 653; Brown et al. *J. Amer. Chem. Soc.* 1971, 93, 1818; *J. Organomet Chem.* 1971, 32, C1; *J. Amer. Chem. Soc.* 1970, 92, 6648), which are able to undergo addition onto alkenes (hydroboration see H.C. Brown, *Hydroboration;* Benjamin, N.Y., 1962; *Boranes in Organic Chemistry;* Cornell University Press, Ithaca, N.Y., 1972; A. Pelter, K. Smith and H. C. Brown, *Borane Reagents;* Academic Press, London, 1988). In the reaction depicted below a linear alkadiene is used as the substrate, although other dienes (internal, cyclic, etc.) can also be used in this reaction.

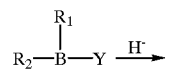

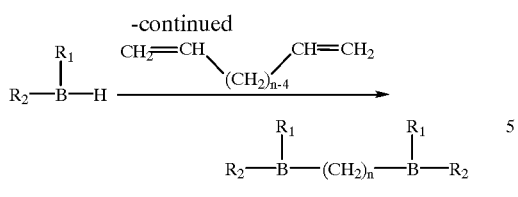

The radicals $R_1$ and $R_2$ are as defined above. Here too it is also possible to obtain isomeric forms or mixtures.

Poly(dialkoxyboryl), poly(diaryloxyboryl) or poly(dihaloboryl) compounds are obtainable, for example, by the reaction of a dimetallated compound (Negishi et al. *J. Org. Chem.* 1990, 55, 5406) with a trialkoxy- or triaryloxyborane (Brown et al. *Organometallics* 1983, 2, 1316).

Poly(dialkoxyboryl), poly(diaryloxyboryl) or poly(dihaloboryl) compounds are also obtainable, for example, by the comproportionation of trialkoxy- or triaryloxyboranes (Brown et al. *J. Amer. Chem. Soc.* 1970, 92, 6983; *J. Amer. Chem. Soc.* 1971, 93, 2802) or trihaloboranes (Zakharkin et al. *Izv. Akad. Nauk SSSR* 1962, 12, 2247; K öster et al. *Liebigs Ann. Chem.* 1968, 719, 169; Brown et al. *J. Organomet. Chem.* 1972, 44, 233) with boranes derived from polyenes (Brown, H. C. *Tetrahedron* 1977, 33, 2331; Jadhav et al. *Heterocycles* 1982, 18, 169). The following equation depicts this reaction with a linear-cyclic borane (which can be prepared starting from linear dienes). Alternatively, polymeric, polycyclic, branched, aryl-containing and other boranes are suitable for this reaction.

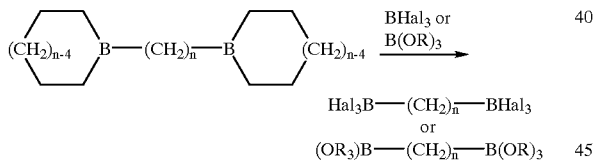

Here again it is possible to obtain isomeric forms or mixtures.

Preference is given to the compounds of the formula I and II in which $R_1$, $R_2$ and $R_3$ independently of one another are unsubstituted phenyl or phenyl which is substituted by unsubstituted or halo-substituted $C_1$–$C_6$alkyl, $OR_6$, $S(O)_p$ $NR_8R_9$ or $C(O)NR_8R_9$;

$R_1'$, $R_2'$, $R_3'$, $R_4$ and $R_5$ have one of the meanings of $R_1$–$R_3$, where the radicals $R_1'$, $R_2'$, $R_3'$, $R_4$ and $R_5$ can also be substituted ortho to the bond to the borate atom;

$R_6$, $R_7$, $R_8$ and $R_9$ are $C_1$–$C_{12}$alkyl or phenyl;

or $R_8$ and $R_9$, together with the nitrogen atom to which they are attached, form a 5- or 6-membered ring which may additionally contain oxygen atoms;

X is $C_1$–$C_{20}$alkylene or is $C_1$–$C_{20}$alkylene interrupted by one or more groups -O-, $SO_2$- or $SiR_{11}'R_{12}'R_{13}'$, or X is an alkylene of the following formulae III–IX:

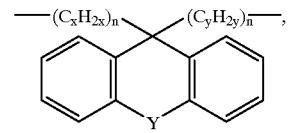

(III)

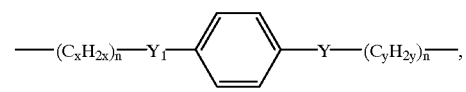

(IV)

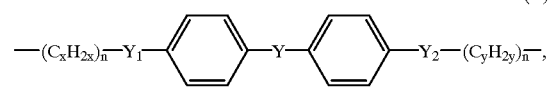

(V)

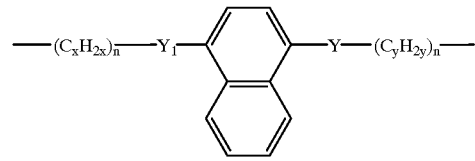

(VI)

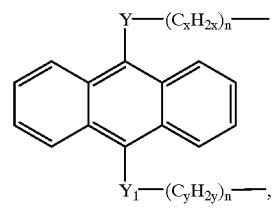

(VII)

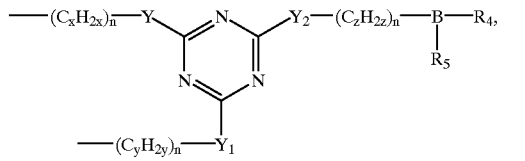

(VIII)

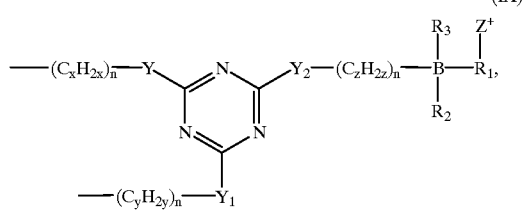

(IX)

in which n is a number from 1 to 6 and the phenyl rings may be substituted by $C_1$–$C_{12}$alkoxy, or X is $C_3$–$C_{12}$cycloalkylene which is unsubstituted or substituted by $(BR_1R_2R_3)^-Z^+$ or $C_1$–$C_{12}$alkyl; and Y, $Y_1$ and $Y_2$ independently of one another are a direct bond or O.

Further compounds of the formula I and II which are of interest are those in which Z is a mono- or divalent dye cation or metal complex, sulfonium, sulfoxonium or iodonium cation, or Z is a UV absorber compound which is able to form cations, or Z is a metal cation of group I of the Periodic Table, or Z is a cation $MY_b^+$, where M is a metal of group II of the Periodic Table and $Y_b$ is alkoxy or halo, or Z is an ammonium salt or phosphonium salt.

Compounds of the formula I which are deserving of emphasis are those in which $R_1$, $R_2$ and $R_3$ are unsubstituted or halo-, $OR_6$- or $C_1$–$C_4$alkyl-substituted phenyl; $R_6$ is $C_1$–$C_4$alkyl; X is $C_2$–$C_6$alkylene, $C_2$–$C_6$alkylene interrupted by phenylene, or $C_6$–$C_{12}$cycloalkylene unsubstituted or substituted by $(BR_1R_2R_3)^-Z^+$; and Z is a tetraalkylammonium or sulfonium cation.

Also of interest are compounds of the formula I in which $R_1$, $R_2$ and $R_3$ are unsubstituted or halo-substituted phenyl; X is a $C_2$–$C_6$alkylene and Z is a tetraalkylammonium cation.

As already mentioned, the compounds of the invention are suitable as coinitiators for the photochemical polymerization of compounds having ethylenically unsaturated double bonds. This photoinitiating effect requires the concomitant use of an electron acceptor compound. Only where the counterion $Z^+$ in the compounds of the formula I of the invention is able to function as an electron acceptor is the addition of a separate electron acceptor compound unnecessary for photocuring.

The invention therefore also provides a photoinitiator comprising (A) at least one compound of the formula I or II as coinitiator and (B) at least one electron acceptor compound, where the electron acceptor compound (B) can also be a constituent of the radical $Z^+$ of the formula I.

The ratio of (A):(B) is for example from 10:1 to 1:10. In order to increase the reactivity it is judicious to add the borate component of the invention (A) in excess; therefore, the ratio of 10:1 is preferred.

If (B) is a constituent of the radical Z in the formula I or II, the ratio of (A):(B) is judiciously 1:1 or 1:0.5 if divalent cationic dye is used as Z.

Alternatively, it is possible in addition to the borates of formula I or II of the invention to add other prior art borate salts to the abovementioned mixtures. These may be either monoborate or bisborate or borate-borane compounds. Appropriate borate salts are described, for example, in U.S. Pat. No. 4,772,530, U.S. Pat. No. 4,772,541, GB 2307473, GB 2307472, GB 2307474 and EP 775706. The borates of the invention can be employed in mixtures, of any desired proportion, with the known borates; for example, in a ratio of from 10:1 to 1:10.

Examples of substances employed as electron acceptor compounds (B) are sensitizers, such as thioxanthones, camphorquinones, reaction accelerators, such as amines, thiols, etc., or dyes or UV absorbers. Other examples of suitable electron acceptor compounds are transition metal complex compounds or dyes.

Suitable transition metal complex compounds are described, for example, in U.S. Pat. No. 4,954,414; examples are bis(2,2'-bipyridine)(4,4'-dimethyl-2,2'-bipyridine)ruthenium, tris(4,4'-dimethyl-2,2'-bipyridine)ruthenium, tris(4,4'-dimethyl-2,2'-bipytidine)iron, tris(2,2', 2"-terpyridine)ruthenium, tris(2,2'-bipyridine)ruthenium and bis(2,2'-bipyridine)-(5-chloro-1,10-phenanthroline)ruthenium.

Suitable dyes which can be added as electron acceptor compounds are described, for example, in U.S. Pat. No. 5,151,520. These are, for example, triarylmethane, such as Malachite Green, indolines, thiazines, for example Methylene Blue, xanthones, thioxanthones, oxazines, acridines or phenazines, for example safranin.

Particularly suitable dyes are Malachite Green, Methylene Blue, Safranin O, rhodamines of the formula

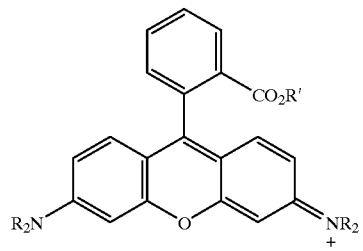

in which R is alkyl or aryl radicals and R' is hydrogen, an alkyl or aryl radical, examples being Rhodamine B, Rhodamine 6G or Violamine R, and also Sulforhodamine B or Sulforhodamine G.

Other suitable dyes are neutral dyes, such as fluorones as are described by Neckers et al. in J. Polym. Sci., Part A, Poly. Chem, 1995, 33, 1691–1703.

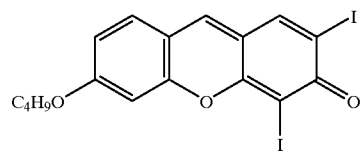

is of particular interest, as are other neutral dyes.

Examples of further suitable dyes are cyanines of the formula

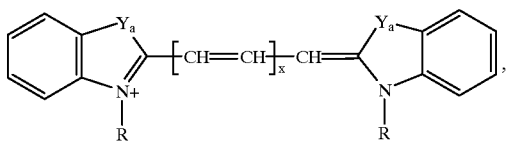

in which R=alkyl; x=0,1,2,3 or 4 and $Y_a$=CH=CH, N—$CH_3$, $C(CH_3)_2$, O, S, Se. Preferred cyanines are those in which $Y_a$ in the above formula is $C(CH_3)_2$ or S.

Also suitable are dyes which absorb in the IR region, such as those, for example, that are described in EP 438123.

The following dye compounds, moreover, are suitable:

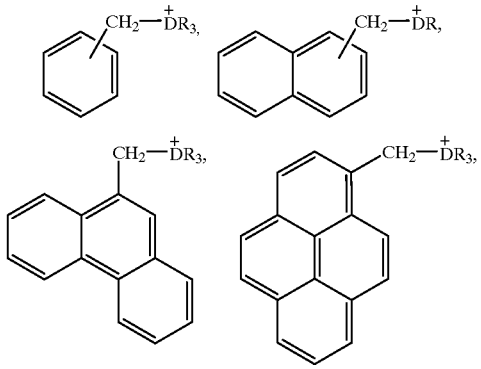

in which D is P, N or S and R is an alkyl or aryl radical. Preferred compounds are those of the above formula in which $DR_3$ is $N(CH_3)_3$, $N(C_2H_5)_3$ or $P(C_6H_5)_3$.

Likewise suitable are compounds such as

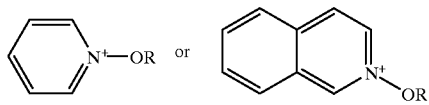

as described, for example, by Yagci et al. in J. Polym. Sci. Part A: Polymer Chem. 1992, 30, 1987 and Polymer 1993, 34(6), 1130 or those such as

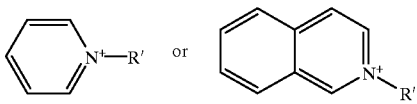

where R'=unsubstituted or substituted benzyl or phenacyl, described in JP-A Hei 7 70221. The abovementioned pyridinium compounds may also be substituted in the aromatic pyridinium ring.

Other suitable dyes can be found, for example, in U.S. Pat. No. 4,902,604. These are azulene dyes. Of particular interest as component (B) for the photoinitiators of the invention are the compounds 1–18 indicated in the table in columns 10 and 11 of that patent. Examples of further suitable dyes are merocyanine dyes as described, for example, in U.S. Pat. No. 4,950,581 from column 6, line 20 to column 9, line 57.

Additionally suitable as component (B) are O-alkylated aromatic nitrogen-heterocyclic amine oxide cation salts (quinolinium salts), e.g. dyes of the formula XX

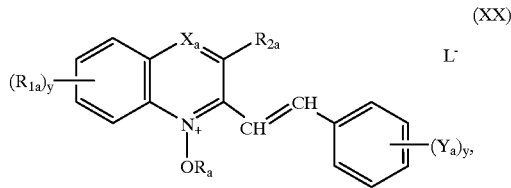

(XX)

in which $X_a$ is CH, C—CH$_3$, C—Cl, C—O—C$_1$–C$_8$alkyl or N;
$R_a$ is C$_1$–C$_6$alkyl, benzyl, CH$_2$COOR$_{3a}$ or a radical

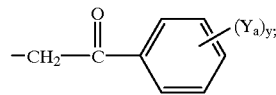

$R_{1a}$ is C$_1$–C$_8$alkoxy, C$_1$–C$_{12}$alkyl, halo, NO$_2$, benzyloxy or phenyloxy, where the phenyl ring in the benzyloxy or phenyloxy radical is unsubstituted or substituted by C$_1$–C$_{12}$alkyl, C$_1$–C$_6$alkoxy, halo or CF$_3$;
$R_{2a}$ is C$_1$–C$_8$alkoxy, C$_1$–C$_{12}$alkyl, benzyloxy or phenyloxy, where the phenyl ring in the benzyloxy or phenyloxy radical is unsubstituted or substituted by C$_1$–C$_{12}$alkyl, C$_1$–C$_6$alkoxy, halo or CF$_3$;
$R_{3a}$ is hydrogen, C$_1$–C$_{12}$alkyl or benzyl;
$Y_a$ is unsubstituted or C$_1$–C$_6$alkoxy-substituted C$_1$–C$_6$alkyl, or $Y_a$ is C$_1$–C$_6$alkoxy, halo, CF$_3$, NO$_2$, CF$_3$O, benzyloxy or phenyloxy, where the phenyl ring in the benzyloxy or phenyloxy radical is unsubstituted or substituted by C$_1$–C$_{12}$alkyl, C$_1$–C$_6$alkoxy, halo or CF$_3$, or, if y is two and both substituents $Y_a$ are alkoxy, these alkoxy radicals can form a dioxolane or dioxane ring which is fused to the phenyl ring of the styryl radical;
y is 1 to 4, preferably 1; and
L is an anion.

If y>1, the y radicals $R_{1a}$ can be different. The same applies for y radicals $Y_a$. Moreover, the numerical values for the index y in this application for the group $(Y_a)_y$ and $(R_{1a})_y$ are to be regarded as independent of one another.

The cation of the above formula can also be the radical $Z^+$ in the compounds of the formulae I and II.

The compounds are prepared by 1. oxidation of an aromatic nitrogen-heterocyclic compound having a methylene radical in one or more of positions 2, 4 and 6, relative to the ring nitrogen, to give the amine oxide; 2. reaction of the amine oxide with $Y_a$-substituted benzaldehyde, catalysed by alkali; 3. alkylation of the resulting product. Similar compounds as well as their preparation are, for example, described in WO 97/42227.

As component (B) for the compounds or photoinitiators of the invention it is also possible to use coumarin compounds. Examples thereof are given in U.S. Pat. No. 4,950,581 in column 11, line 20 to column 12, line 42.

Also suitable as component (B) is camphorquinone, and derivatives thereof.

Other suitable components (B) are xanthones or thioxanthones as described, for example, in U.S. Pat. No. 4,950,581, column 12, line 44 to column 13, line 15.

Neutral dyes are also suitable as component (B).

As component (B) it is also possible to employ anionic dye compounds. Suitable examples include Rose Bengal, eosine or fluorescein. Further suitable dyes, from the triarylmethane or azo class, for example, are given, for example, in U.S. Pat. No. 5,143,818. Examples are Ethyl Orange (Chem. Abstr. Reg. No. 62758-12-7), Brilliant Blue G (Chem. Abstr. Reg. No. 6104-58-1), Brilliant Blue R (Chem. Abstr. Reg. No.6104-59-2), Lissamine Green B (Chem. Abstr. Reg. No. 3087-16-9) or Patent Blue VF (Chem. Abstr. Reg. No.129-17-9).

Preferred photoinitiators of the invention are those in which the electron acceptor compound (B) is a dye or UV absorber. Of particular interest are those photoinitiators in which the UV absorber is a thioxanthone derivative, coumarin, benzophenone, a benzophenone derivative or a hexaarylbisimidazole derivative, and those in which the dye is a cyanine dye or a dye which loses or changes its colour in the course of irradiation.

Examples of such colour-changing dyes are cyanine dyes and pyrylium dyes or the above-described O-alkylated aromatic nitrogen-heterocyclic amine oxide cation salts (quinolinium salts).

Suitable hexaarylbisimidazole derivatives are described, for example, in U.S. Pat. Nos. 3,784,557, 4,252,887, 4,311, 783, 4,459,349, 4,410,621 and 4,622,286. Of particular interest are 2-o-chlorophenyl-substituted derivatives, such as 2,2'-bis(o-chlorophenyl)-4,4',5,5'-tetraphenyl-1,1'-bisimidazole. Other UV absorbers which are suitable in this context are, for example, polycyclic aromatic hydrocarbons, such as anthracene or pyrene, and the triazines described in EP 137452, DE 2718254 and DE 2243621. Further suitable triazines are given in U.S. Pat. No. 4,950,581, column 14, line 60 to column 18, line 44. Of special interest are trihalomethyltriazines, such as 2,4-bis(trichloromethyl)-6-(4-styrylphenyl)-s-triazine. Further suitable electron acceptors (B) are benzopteridinediones (described in JP Hei 02 113002), substituted benzophenones (e.g. Michler's ketone, QUANTACURE ABQ, QUANTACURE BPQ and QUAN- TACURE BTC from International Biosynthetics), trichloromethyltriazines (described in JP Hei 01 033548), metal complexes (described in JP Hei 04 261405), porphyrins (described in JP Hei 06 202548 and JP Hei 06 195014), coumarins and ketocoumarins (described in U.S. Pat. No. 4,950,581 and JP Hei 06 175557), p-aminophenyl compounds (described in EP 475 153), xanthenes (described in JP Hei 06 175566) or pyrylium, thiopyrylium and selenopyrylium dyes (described in JP Hei 06 175563).

In addition to the coinitiator (A), the photoinitiator systems of the invention may also comprise further borate salts (Al) as coinitiators.

Such borates are known from the prior art. For instance, examples of suitable coinitiators $A_1$ are compounds of the formula XXI and XXIa

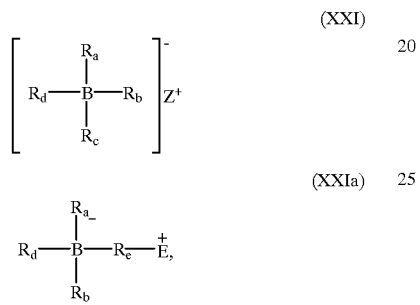

in which $R_a$, $R_b$, $R_c$ and $R_d$ independently of one another are phenyl or another aromatic hydrocarbon, with or without heteroatoms, where these aromatic radicals are unsubstituted or substituted 1–5 times by unsubstituted or $OR_{23}$- or $R_{24}R_{25}N$-substituted $C_1$–$C_{20}$alkyl, or by $C_2$–$C_{20}$alkyl, which may be interrupted by one or more radicals O, $S(O)_p$ or $NR_{26}$, or the aromatic radicals are substituted by $OR_{23}$, $R_{23}S(O)_p$, $R_{23}S(O)_2O$, $R_{24}R_{25}N$, $R_{23}OC(O)$, $R_{24}R_{25}NC(O)$, $R_{27}C(O)$, $R_{27}R_{28}R_{29}Si$, $R_{27}R_{28}R_{29}Sn$, halo, CN, $R_{27}R_{28}P(O)_q$, CN and/or

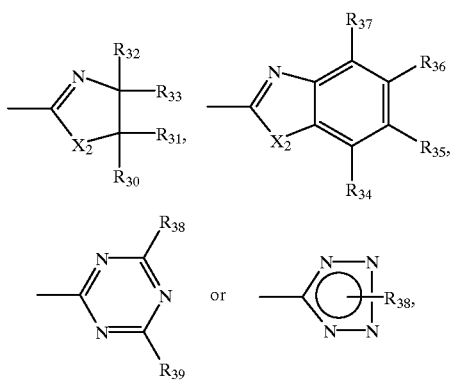

or the radicals $R_b$ and $R_c$ form bridged structures of the formulae XXII, XXIIa or XXIIb

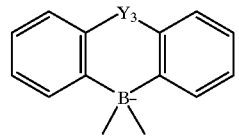

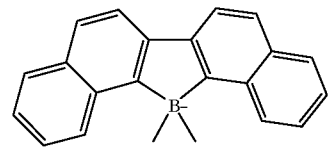

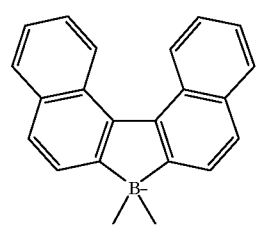

whose aromatic rings are unsubstituted or substituted by $C_1$–$C_{20}$alkyl, by $C_2$–$C_{20}$alkyl which is interrupted by one or more radicals O, $S(O)_p$ or $NR_{26}$, or the aromatic rings are substituted by $OR_{23}$, $R_{23}S(O)_p$, $R_{23}S(O)_2O$, $R_{24}R_{25}N$, $R_{23}OC(O)$, $R_{24}R_{25}NC(O)$, $R_{27}C(O)$, $R_{27}R_{28}R_{29}Si$, halo, CN, $R_{27}R_{28}P(O)_q$ and/or $R_{27}R_{28}R_{29}Sn$, or $R_a$, $R_b$, $R_c$ and $R_d$ independently of one another are $R_{27}R_{28}R_{29}Si$, or $R_a$, $R_b$, $R_c$ and $R_d$ independently of one another are $C_1$–$C_{20}$alkyl, $C_2$–$C_{20}$alkyl which is interrupted by one or more radicals O, $S(O)_p$ or $NR_{26}$, or are $C_3$–$C_{12}$cycloalkyl, $C_2$–$C_8$alkenyl, phenyl-$C_1$–$C_6$alkyl or naphthyl-$C_1$–$C_3$alkyl, where the radicals $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl are unsubstituted or substituted by $OR_{23}$, $R_{23}S(O)_p$, $R_{23}S(O)_2O$, $R_{24}RN$, $R_2R_{24}RNC(O)$, $R_{27}C(O)$, $R_{27}R_{28}RaSi$, $R_{27}R_{28}R_{29}Sn$, halo, $R_{27}R_{28}P(O)_q$, and/or CN;

$R_e$ is a divalent aromatic hydrocarbon radical which is unsubsfituted or substituted by $C_1$–$C_6$alkyl, $OR_{23}$, $R_{23}S(O)_p$, $R_{23}S(O)_2O$, $R_{24}R_{25}N$, $R_{23}OC(O)$, $R_{24}R_{25}NC(O)$, $R_{27}C(O)$, $R_{27}R_{28}R_{29}Si$, CN or halo, or $R_e$ is phenyl-$C_1$–$C_6$alkylene;

E is $R_{44}R_{45}$, $R_{46}P$, $R_{23}R_{24}R_{25}N$ or $R_{23a}S$;

$R_{44}$, $R_{45}$, and $R_{46}$ independently of one another are $C_1$–$C_{12}$alkyl, $C_2$–$C_{12}$alkenyl or $C_3$–$C_{12}$cycloalkyl, where the radicals $C_1$–$C_{12}$alkyl, $C_2$–$C_{12}$alkenyl and $C_3$–$C_{12}$cycloalkyl are unsubstituted or substituted by $R_{23}OCO$ or CN, or $R_{44}$, $R_{45}$ and $R_{46}$ are unsubstituted or mono- to penta-$C_1$–$C_6$alkyl-, -$C_1$–$C_{12}$alkoxy- or -halo-substituted phenyl-$C_1$–$C_6$alkyl, or $R_{44}$, $R_{45}$ and $R_{46}$ are unsubstituted or mono- to penta-$C_1$–$C_6$alkyl-, -$C_1$–$C_{12}$alkoxy- or -halo-substituted phenyl;

$Y_3$ is $(CH_2)_r$, CH=CH, C(O), $NR_{26}$, O, $S(O)_p$—$CR_{42}R_{43}$-,

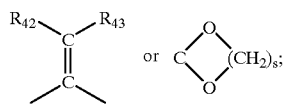

r is 0, 1, 2 or 3;

s is 2 or 3;

p is 0, 1 or 2;

q is 0 or 1;

$R_{23}$ and $R_{23a}$ independently of one another are unsubstituted or halo-substituted $C_1$–$C_{12}$alkyl, phenyl-$C_1$–$C_6$alkyl or phenyl, where the radicals phenyl-$C_1$–$C_6$alkyl or phenyl are unsubstituted or substituted 1 to 5 times by $C_1$–$C_6$alkyl, $C_1$–$C_{12}$alkoxy and/or halo;

$R_{24}$ and $R_{25}$ independently of one another are hydrogen, unsubstituted or $C_1$–$C_{12}$alkoxy-, halo-, OH-, COOR$_{23}$- or CN-substituted $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or substituted 1–5 times by $C_1$–$C_6$alkyl, $C_1$–$C_{12}$alkoxy and/or halo, or $R_{24}$ and $R_{25}$, together with the nitrogen atom to which they are attached, form a 5- or 6-membered ring which may additionally contain oxygen or sulfur atoms;

$R_{26}$ is hydrogen, $C_1$–$C_{12}$alkyl, phenyl-$C_1$–$C_6$alkyl or phenyl, where the radicals phenyl-$C_1$–$C_6$alkyl or phenyl are unsubstituted or substituted 1–5 times by $C_1$–$C_6$alkyl, $C_1$–$C_{12}$alkoxy and/or halo;

$R_{27}$, $R_{28}$ and $R_{29}$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halo;

$R_{30}$, $R_{31}$, $R_{32}$ and $R_{a3}$ independently of one another are hydrogen, unsubstituted or $C_1$–$C_{12}$alkoxy-substituted $C_1$–$C_{12}$alkyl, unsubstituted or mono- to penta-$C_1$–$C_6$alkyl-, -$C_1$–$C_{12}$alkoxy- or -halo-substituted phenyl-$C_1$–$C_6$alkyl or are unsubstituted or mono- to penta-$C_1$–$C_6$alkyl-, -$C_1$–$C_{12}$alkoxy- or -halo-substituted phenyl, or two of the radicals $R_{30}$, $R_{31}$, $R_{32}$ and $R_{33}$ together form an aromatic ring to which further rings may be fused;

$R_{34}$, $R_{35}$, $R_{36}$, $R_{37}$, $R_{38}$ and $R_{39}$ independently of one another are hydrogen, unsubstituted or $C_1$–$C_{12}$alkoxy-, OH- or halo-substituted $C_1$–$C_{12}$alkyl, or are unsubstituted or $C_1$–$C_{12}$alkyl-, $C_1$–$C_{12}$alkoxy-, OH- or halo-substituted phenyl;

$R_{42}$ and $R_{43}$ are $C_1$–$C_6$alkyl or phenyl, or $R_{42}$ and $R_{43}$, together with the carbon atom to which they are attached, form a 5- or 6-membered ring;

$X_2$ is N, S or O; and

Z is a radical which is able to form positive ions.

Examples of compounds of the formula XXI and XXIa and their preparation are disclosed in GB 2307472, GB 2307473 and GB 2307474.

It is also possible to employ bisborate salts as described, for example, in EP 775706, as coinitiators (A).

Further examples of compounds of the formulae XXI and XXIa can be found in U.S. Pat. No. 5,176,984, U.S. Pat. No. 5,151,520, U.S. Pat. No. 5,100,755, U.S. Pat. No. 5,057,393, U.S. Pat. No. 5100755, U.S. Pat. No. 4,954,414 and U.S. Pat. No. 4,772,530, EP 710887, U.S. Pat. No. 3,567,453, U.S. Pat. No. 4,343,891, EP 109772, EP 109773, JP Kokai Hei 5-255347, JP Kokai Hei 2-108055, U.S. Pat. No. 5,168,032, EP 726497, JP Kokai Hei 4-146905, JP Kokai Hei 4-261405 and JP Kokai Hei 5-61247.

In accordance with the invention, the photoinitiators can be used for the photopolymerizaion of ethylenically unsaturated compounds and of mixtures which comprise such compounds. This use can also be practiced in combination with another photoinitiator and/or other additives.

The invention therefore also provides photopolymerizable compositions comprising (a) at least one ethylenically unsaturated photopolymerizable compound and (b) at least one photoinitiator as described above, and in addition to components (a) and (b) possibly other photoinitiators (c) and/or further additives (d) as well.

Specific examples of such additional photoinitiators and additives are given later on below.

As already mentioned, it is advantageous to combine the borate compounds of the formula I or II of the invention with sensitizers (i.e. energy transfer agents). In this context, highly effective combinations include, in particular, those with two or more different sensitizers, such as mixtures of the borate compounds of the invention with onium salts and thioxanthones or coumarins or dyes. Preferred onium salts in these mixtures are diphenyliodonium hexafluorophosphate, (p-octyloxyphenyl)(phenyl)iodonium hexafluorophosphate, or corresponding other anions of these compounds, such as the halides, for example; and, in addition, sulfonium salts, such as triarylsulfonium salts (CYRACURE® UVI 6990, CYRACURE® UVI-6974 from Union Carbide; DEGACURE® KI 85 from Degussa or SP-150 and SP-170 from Asahi Denka). Preference is given, for example, to a mixture of the borate compounds of the invention with diaryliodonium hexafluorophosphate and isopropylthioxanthone, to a mixture of the borate compounds of the invention with (p-octyloxyphenyl)(phenyl)iodonium hexafluorophosphate and isopropylthioxanthone, and to a mixture of the borate compounds of the invention with CYRACURE® UVI-6974 and isopropylthioxanthone (CYRACURE® UVI-6974=

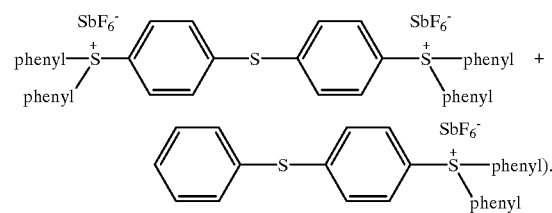

However, it is particularly advantageous to add yet another photoinitiator, of the α-amino ketone type, to the abovementioned mixtures. For example, mixtures of the borates of the invention with onium salts and thioxanthones or dyes and α-amino ketones are highly effective. A preferred example is the mixture of the borate compounds of the invention with diaryliodonium hexafluorophosphate or (p-octyloxyphenyl)(phenyl)iodonium hexafluorophosphate, isopropylthioxanthone and (4-methylthiobenzoyl)methyl-1-morpholinoethane.

The invention therefore additionally provides a composition comprising in addition to components (a) and (b) at least one neutral, anionic or cationic dye or a thioxanthone compound and an onium compound.

The abovementioned onium compounds are preferred.

The invention additionally provides a composition comprising in addition to components (a) and (b) at least one neutral, anionic or cationic dye and an onium compound and a free-radical photoinitiator (d), especially an α-amino ketone compound.

The photoinitiator systems of the invention may additionally comprise various other components such as, for example, various combinations of the components (1) to (8), which are described in detail in EP 747771:

(1) compounds having a carbon-halogen bond;
(2) α-amino ketone compounds;
(3) keto oxime compounds;
(4) organic peroxides;
(5) thio compounds;
(6) hexaarylbisimidazole compounds;
(7) aromatic onium salt compounds;
(8) keto oxime ester compounds.

The unsaturated compounds may include one or more olefinic double bonds. They may be of low (monomeric) or high (oligomeric) molecular mass. Examples of monomers containing a double bond are alkyl or hydroxyalkyl acrylates or methacrylates, such as methyl, ethyl, butyl, 2-ethylhexyl and 2-hydroxyethyl acrylate, isobornyl acrylate, methyl methacrylate and ethyl methacrylate. Silicone acrylates are also of interest. Other examples are acrylonitrile, acrylamide, methacrylamide, N-substituted (meth) acrylamides, vinyl esters such as vinyl acetate, vinyl ethers such as isobutyl vinyl ether, styrene, alkyl- and halostyrenes, N-vinylpyrrolidone, vinyl chloride and vinylidene chloride.

Examples of monomers containing two or more double bonds are the diacrylates of ethylene glycol, propylene glycol, neopentyl glycol, hexamethylene glycol and of bisphenol A, and 4,4'-bis(2-acryloyloxyethoxy) diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylicized epoxy resins, acrylicized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxide main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxybiphenyl, 2,2-di(4-hydroxy-phenyl)propane, and also novolaks and resols. Examples of polyepoxides are those based on the above-mentioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further suitable polyols are oligoesters having hydroxyl end groups.

Examples of aliphatic and cycloaliphatic polyols are alkylenediols having preferably 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclo-pentanediol, 1,2-, 1,3- or 1,4cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one or with different unsaturated carboxylic acids, and in partial esters the free hydroxyl groups may be modified, for example etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as component (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di(β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis (methacrylamidopropoxy)ethane, β-methacrylamidoethyl methacrylate and N-[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example, 6 to 20 Carbon atoms. Examples of polyurethanes are those composed of saturated or unsaturated diisocyanates and of unsaturated or, respectively, saturated diols.

Polybutadiene and polyisoprene, and copolymers thereof, are known. Examples of suitable comonomers are olefins, such as ethylene, propene, butene and hexene, (meth) acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl alkyl derivatives thereof which are esterified with (meth)acrylic acid, or may be homo- and copolymers of (meth)acrylates which are esterified with hydroxyalkyl (meth)acrylates.

The photopolymerizable compounds can be used alone or in any desired mixtures. It is preferred to use mixtures of polyol (meth)acrylates.

Binders can also be added to the novel compositions, and this is particularly expedient when the photopolymerizable compounds are liquid or viscous substances. The quantity of binder may, for example, be 5–95%, preferably 10–90% and especially 40–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 5000 to 2000000, preferably 10000 to 1000000. Examples are: homo- and copolymers of acrylates and methacrylates, for example copolymers of methyl methacrylatelethyl acrylate/ methacrylic acid, poly (alkyl methacrylates), poly(alkyl acrylates); cellulose esters and cellulose ethers, such as cellulose acetate, cellulose acetate butyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene chloride copolymers, copolymers of vinylidene chloride with acrylonitrile, methyl methacrylate and vinyl acetate, polyvinyl acetate, copoly(ethylenevinyl acetate), polymers such as polycaprolactam and poly (hexamethyleneadipamide), and polyesters such as poly (ethylene glycol terephthalate) and poly(hexamethylene glycol succinate).

The unsaturated compounds can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins. The use of heat-curable resins at the same time is important for use in systems known as hybrid systems, which are photopolymerized in a first stage and then crosslinked by means of thermal aftertreatment in a second stage.

In addition to the photoinitiator (A)/(B) or (c) the photopolymerizable mixtures may include various additives (d). Examples of these are thermal inhibitors, which are intended to prevent premature polymerization, examples being hydroquinone, hydroquinone derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, for example N-diethylhydroxylamine. To exclude atmospheric oxygen during the polymerization it is possible to add paraffin or similar waxlike substances which, being of inadequate solubility in the polymer, migrate to the surface at the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenylbenzophenone, oxalamide or hydroxyphenyl-s-triazine type. These compounds can be used individually or in mixtures, with or without sterically hindered amines (HALS).

Examples of such UV absorbers and light stabilizers are
1. 2-(2'-hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethyl-hexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)-benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy- 5'-(2-isooctyloxycarbonylethyl) phenylbenzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]benzotriazole with polyethylene glycol 300; [R—CH$_2$CH$_2$—COO(CH$_2$)$_3$]$_2$- where R=3'-tert-butyl-4'-hydroxy-5'-2H-benzotriazol-2-yl-phenyl.
2. 2-Hydroxybenzophenones, for example the 4-hydroxy-, 4-methoxy-, 4octoxy-, 4-decyloxy-, 4-dodecyloxy-, 4-benzyloxy-, 4,2',4'-trihydroxy- and 2'-hydroxy-4,4'-dimethoxy derivative.
3. Esters of unsubstituted or substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxy-benzoate, hexadecyl 3,5-di-tert-butyl-4-hydroxybenzoate, octadecyl 3,5-di-tert-butyl-4-hydroxybenzoate and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbomethoxycinnamate, butyl or methyl α-cyano-β-methyl-p-methoxycinnamate, methyl α-carbomethoxy-p-methoxycinnamate and N-(β-carbomethoxy-β-cyanovinyl)-2-methyl-indoline.

5. Sterically hindered amines, for example bis-(2,2,6,6-tetramethylpiperidyl) sebacate, bis-(2,2,6,6-tetramethylpiperidyl) succinate, bis-(1,2,2,6,6-pentamethylpiperidyl) sebacate, bis-(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6,6-tetramethyl-4-piperidyl)hexa-methylene-diamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl)-1,2,3,4-butane tetraoate, 1,1'-(1,2-ethandiyl)bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpiperidyl) 2-n-butyl-2-(2-hydroxy-3,5-di-tert-butylbenzyl) malonate, 3-n-octyl-7,7,9,9-tetramethyl-1,3,8-triazaspiro[4.5]-decane-2,4-dione, bis-(1-octyloxy-2,2,6,6-tetramethylpiperidyl) sebacate, bis-(1-octyloxy-2,2,6,6-tetramethylpiperidyl) succinate, condensation product of N,N'-bis-(2,2,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis-(3-aminopropyl-amino)ethane, condensation product of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-piperidyl)pyrrolidine-2,5-dione and 3-dodecyl-1-(1,2,2,6,6-penta-methyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanalides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyl-oxy-phenyl)-6-(2,4-dimethylphenyl)-1,3,5-triazine, 2-(2-hydroxy-octyloxyphenyl)-4,6-bis(4-methylphenyl)-1,3,5-triazine, 2-(2-hydroxy-4-dodecyloxyphenyl)-4,6-bis(2,4-dimethyl-phenyl)-1,3,5-triazine, 2-[2-hydroxy-4-(2-hydroxy-3-butyloxy-propyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-14-dodecyltridecyl-oxy-(2-hydroxypropyl)oxy-2-hydroxyphenyl)-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bis-isodecyloxy pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis(2,4-di-tert-butylphenyl)-4,4'-biphenylenediphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4di-tert-butyl-6-methylphenyl) methyl phosphite and bis(2,4-di-tert-butyl-6-methylphenyl) ethyl phosphite.

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are, for example, thiols, thioethers, disulfides and phosphines, as described, for example, in EP 438123 and GB 2180358.

The curing process can be assisted, in particular, by compositions which are pigmented (for example with titanium dioxide), and also by adding a component which under thermal conditions forms free radicals, for example an azo compound such as 2,2'-azobis- (4-methoxy- 2,4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

Further customary additives, depending on the intended use, are optical brighteners, fillers, pigments, dyes, wetting agents or levelling assistants.

In order to cure thick and pigmented coatings it is appropriate to add glass microspheres or pulverized glass fibres, as described for example in U.S. Pat. No. 5,013,768.

The amount of the additional additives (d) used depends on the particular intended use of the composition and is within the customary range known to the skilled worker.

The invention also provides compositions comprising as component (a) at least one ethylenically unsaturated photopolymerizable compound which is emulsified or dissolved in water.

Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are mono- or polyfunctional, ethylenically unsaturated prepolymers which are known per se for aqueous prepolymer dispersions, can be initiated by free radicals and have a content of, for example, from 0.01 to 1.0 mol of polymerizable double bonds per 100 g of prepolymer and an average molecular weight of, for example, at least 400, in particular from 500 to 10 000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth)acrylates and of acrylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth)acrylate polymers, are described in EP 41125, and suitable water-dispersible, radiation-curable prepolymers of urethane acrylates can be found in DE 2936039.

Further additives which may be included in these radiafton-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, matting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone and cellulose ethers. Emulsifiers which can be used are nonionic emulsifiers and, if desired, ionic emulsifiers as well.

The quantity of photoinitiator in the photopolymerizable compositions is expediently from 0.05 to 15% by weight, preferably from 0.1 to 5% by weight, based on the composition. By photoinitiator is meant here all of the photoinitiators present in the composition, in other words component (b) and also, if present, additional photoinitiators (c).

In certain cases it may be of advantage to use mixures of two or more of the photoinitiators of the invention. As already mentioned above, it is of course also possible to use mixtures with other known photoinitiators, for example mixtures with benzophenone, benzophenone derivatives, acetophenone, acetophenone derivatives, for example α-hydroxycycloalkyl phenyl ketones, phenylglyoxalates, dialkoxyacetophenones, α-hydroxy- or α-aminoacetophenones, 4-aroyl-1,3-dioxolanes, benzoin alkyl ethers and benzil ketals, camphorquinones, mono-, bis- and trisacylphosphine oxides, titanocenes or ferrocenes.

Examples of particularly suitable photoinitiators are: 1-(4-dodecylbenzoyl)-1-hydroxy-1-methylethane, 1-(4-isopropylbenzoyl)-1-hydroxy-1-methylethane, 1-benzoyl-1-hydroxy-1-methylethane, 1-[4-(2-hydroxyethoxy)benzoyl]-1-hydroxy-1-methylethane, 1-[4-(acryloyloxyethoxy)benzoyl]-1-hydroxy-1-methylethane, diphenyl ketone, phenyl 1-hydroxy-cyclohexyl ketone, (4-morpholinobenzoyl)-1-benzyl-1-dimethylaminopropane, 1-(3,4-di-methoxyphenyl)-2-benzyl-2-dimethylamino-butan-1-one, (4-methylthiobenzoyl)-1-methyl-1-morpholinoethane, benzil dimethyl ketal, bis (cyclopentadienyl)bis(2,6-difluoro-3-pyrryl-phenyl) titanium, cyclopentadienyl-arene-iron(II) complex salts, for example ($\eta^6$-iso-propylbenzene)($\eta^5$-cyclopentadienyl)iron (II) hexafluorophosphate, trimethylbenzoyidiphenylphosphine oxide, bis(2,6-dimethoxybenzoyl)-(2,4,4-trimethylpentyl)phosphine oxide, bis(2,4,6-trimethylbenzoyl)-2,4-dipentoxyphenylphosphine oxide or bis(2,4,6-trimethylbenzoyl)phenyl-phosphine oxide. Other suitable additional photoinitiators can be found in U.S. Pat. No. 4,950,581 column 20, line 35 to column 21, line 35.

Also suitable are triazine compounds, for example the triazines described in EP 137452, in DE 2718254 and in DE 2243621. Further suitable triazines can be found in U.S. Pat. No. 4,950,581, column 14, line 60 to column 18, line 44. There is particular interest in trihalomethyltriazines, for example 2,4-bis(trichloromethyl)-6-(4-styrylphenyl)-s-triazine.

Where the novel photoinitiators are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17–25), aromatic sulfonium, phosphonium or iodonium salts (as described for example in U.S. Pat. No. 4,950,581, column 18, line 60 to column 19, line 10) or cyclopenta-dienyl-arene-iron(II) complex salts, for example ($\eta^6$-isopropylbenzene)-($\eta^5$-cyclopentadienyl)iron(II) hexafluorophosphate, oxime sulfonates, as described for example in EP 780729 or EP 571330, or disulfones or imido sulfonates such as

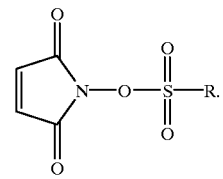

Compositions comprising as additional photoinitiator (c) a titanocene, a ferrocene, a benzophenone, a benzoin alkyl ether, a benzil ketal, a 4-aroyl-1,3-dioxolane, a dialkoxyacetophenone, an α-hydroxy- or α-aminoacetophenone, an α-hydroxycycloalkyl phenyl ketone, a phenylglyoxalic ester or derivatives thereof, a xanthone, a thioxanthone, an anthraquinone or a mono-, bis- or trisacylphosphine oxide, or mixtures thereof, as additional photoinitiator, especially an α-amino ketone, are of particular interest.

Also of interest are compositions in which as further additive (d) a readily reducible compound, especially a halogenated hydrocarbon is used.

Suitable readily reducible compounds are, for example, halogenated hydrocarbons such as, in particular,

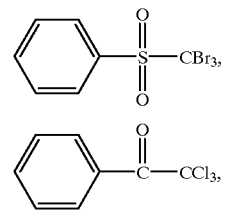

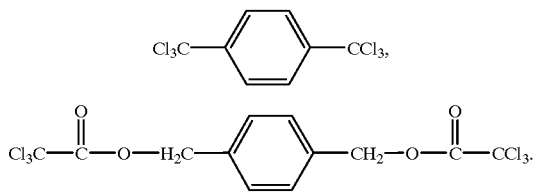

The term readily reducible compound is to be understood in this context as including compounds as described in U.S. Pat. No. 4,950,581, examples including iodonium salts, sulfonium salts, and other onium salt compounds (as described for example in EP 726497), organic peroxides, compounds having carbon-halide bonds (trichloromethyltriazines), heterocyclic sulfur compounds, and other photoinitiators (α-amino ketones). Examples of other additives are heterocycles as described in the Patents and Patent Applications U.S. Ser. No. 5168032, JP 02 244050, JP 02 054268, JP 01017048 and DE 383308.

Examples of further additives are aromatic imines, described in U.S. Pat. No. 5,079,126, and aromatic diazo compounds, described in U.S. Pat. No. 5,200,292 (e.g. iminoquinone diazides), thiols, described in U.S. Pat. No. 4,937,159 and thiols and N,N-dialkylanilines, described in U.S. Pat. No. 4,874,685. It is also possible to employ two or more of the stated electron acceptors and additives in combination.

The photopolymerizable compositions can be used for various purposes, for example as printing ink, as a clear finish, as a white finish, for example for wood or metal, as a coating material, inter alia for paper, wood, metal or plastic, as a powder coating, as a daylight-curable coating for roadmarking and the marking of buildings, for photographic reproduction techniques, for holographic recording materials, for image recording techniques or for producing printing plates which can be developed with organic solvents or with aqueous alkalis, for producing masks for screen printing, as dental filling compositions, as adhesives, including pressure-sensitive adhesives, as laminating resins, as etch resists or permanent resists, and as solder masks for electronic circuits, as photostructurable dielectrics, for producing three-dimensional articles by mass curing (UV curing in transparent moulds) or by the stereolithography technique, as is described, for example, in U.S. Pat. No. 4,575,330, for producing composite materials (for example styrenic polyesters, which may if desired contain glass fibres and/or other fibres and other auxiliaries) and other thick-layered compositions, for producing optical switches, waveguides and optical gratings (e.g. interference gratings), for producing optical lenses (e.g. contact lenses, Fresnel lenses), for coating or sealing electronic components, or as coatings for optical fibres.

The compounds of the invention may additionally be employed as initiators for emulsion, bead or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent.

Unsaturated polyester resins are usually used in two-component (two-pack) systems together with a monounsaturated monomer, preferably with styrene. For photoresists, specific one-component systems are often used, for example polymaleimides, polychalcones or polyimides, as described in DE 2308830.

The compounds of the invention and mixtures thereof can also be used as free-radical photoinitiators or photoinitiating systems for radiatton-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting of the powder particles can be delayed if desired in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics.

In addition to the novel photoinitiators, the powder coating formulations may also include UV absorbers. Appropriate examples are listed above in sections 1.–8.

The photocurable compositions of the invention are suitable, for example, as coating materials for substrates of all kinds, for example wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate a reproduced image.

Coating of the substrates can be carried out by applying to the substrate a liquid composition, a solution or a suspension. The choice of solvent and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 $\mu$m to more than 100 $\mu$m.

The radiation-sensitive compositions of the invention find application as negative resists, having a very high photosensitivity and being able to be developed in an aqueous alkaline medium without swelling. They are suitable as photoresists for electronics (electroplating resist, etch resist, solder resist), for the production of printing plates, such as offset, flexographic and relief printing plates or screen printing for the production of inking stamps, for use in chemical milling or as a microresist in the production of integrated circuits. The formulations can additionally be used as photostructurable dielectrics, encapsulation materials and insulating layers in the production of computer chips, circuit boards and other electrical or electronic components. The compounds of the invention can be employed in particular in systems which comprise not only the free-radically polymerizable components but also polyimide precursors (described, for example, in EP 119162). The possible layer supports, and the processing conditions of the coated substrates, are just as varied.

The compositions and compounds of the invention are also used to produce single-layer or multilayer materials for image recording or image reproduction (copying, repography), which may be in one or more colours. These materials can also be employed in colourproofing systems. For this technology it is also possible to employ formulations which comprise microcapsules, and a thermal step may follow the exposure step for producing the image. Such systems and technologies, and their application, are described, for example, in U.S. Pat. No. 5,376,459.

Substrates used for photographic information recording include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes are generally from about 0.5 $\mu$m to 10 $\mu$m, while for printed circuits they are from 1 $\mu$m to about 100 $\mu$m.

Following the coating of the substrates, the solvent is removed, generally by drying, to leave a coat of the photoresist on the substrate.

The term "imagewise" exposure includes both exposure through a photomask comprising a predetermined pattern, for example a slide, exposure by means of a laser beam, which for example is moved under computer control over the surface of the coated substrate and in this way produces an image, and irradiation with computer-controlled electron beams. It is also possible to use masks formed from liquid crystals, which are driven pixel by pixel in order to generate digital images, as is described, for example, by A. Bertsch, J. Y. Jezequel, J. C. Andre in Journal of Photochemistry and Photobiology A: Chemistry 1997, 107, pp. 275–281 and by K.-P. Nicolay in Offset Printing 1997, 6, pp. 34–37.

Following the imagewise exposure of the material and prior to development, it may be advantageous to carry out thermal treatment for a short time. In this case only the exposed sections are thermally cured. The temperatures employed are generally 50–150° C., preferably 80–130° C.; the period of thermal treatment is in general between 0.25 and 10 minutes.

The photocurable composition may additionally be used in a process for producing printing plates or photoresists as is described, for example, in DE-A40 13 358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the compositions of the invention can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printing inks, since the drying time of the binder is a critical factor for the production rate of graphic products, and should be in the order of magnitude of fractions of seconds. UV-curable inks are particularly important for screen and offset printing. The compounds of the invention can also be used in UV-curing inkjet inks.

As already mentioned above, the mixtures of the invention are also highly suitable for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Another field where photocuring is employed is the coating of metals, in the case, for exampie, of the coating of metal plates and tubes, cans or bottle caps, and photocuring of polymer coatings, for example of floor or wall coverings based on PVC.

Examples of the photocuring of paper coatings are the colourless varnishing of labels, record sleeves and book covers.

It is also possible to employ the compounds of the invention in toners for xerography, in order to fix them.

Also of interest is the use of the compounds of the invention for curing shaped articles made from composite compositions. The composite composition consists of a self-supporting matrix material, for example a glass fibre fabric, or alternatively, for example, plant fibres [cf. K.-P. Mieck, T. Reussmann in Kunststoffe 85 (1995), 366–370], which is impregnated with the photocuring formulation. Shaped parts comprising composite compositions, when produced using the compounds of the invention, attain a high level of mechanical stability and resistance. The compounds of the invention can also be employed as photocuring agents in moulding, impregnating and coating compositions as are described, for example, in EP 7086. Examples of such compositions are fine coat resins, which are subject to stringent requirements regarding curing activity and yellowing resistance, and fibre-reinforced mouldings, such as, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstarkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The photocurable compositions of the invention can also be used for casting resins or for embedding articles, for example electronic components, etc. They can additionally be employed for lining cavities and pipes. Curing is carried out using medium-pressure mercury lamps as are conventional in UV curing. However, there is also particular interest in less intense lamps, for example of the type TL 40W/03 or TL 40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds of the invention can also be used to produce holograms, optical wave guides and optical switches, utilizing the generation of a difference in the refractive index between exposed and unexposed regions.

The use of photocurable compositions for imaging techniques and for the optical production of information carriers is also important. In such applications, as already described above, the layer (wet or dry) applied to the support is irradiated through a photomask with UV or visible light, and the unexposed areas of the layer are removed by treatment with a solvent (=developer). Application of the photocurable layer to metal can also be carried out by electro-deposition. The exposed areas are polymeric through crosslinking and are therefore insoluble and remain on the support. Appropriate coloration produces visible images. Where the support is a metallized layer, the metal can, following exposure and development, be etched away at the unexposed areas or reinforced by electroplating. In this way it is possible to produce printed electronic circuits and photoresists.

The compounds and photoinitiator systems of the invention can also be used as toners in a formulation as described, for example, in JP Kokai Hei 7-140718.

Furthermore, the compounds and photoinitiator systems of the invention can be used for de-colouring coloured materials, as is described, for example, in JP Kokai Hei 6-299106, or for the photobleaching of image recording materials, as is described, for example, in JP Kokai Hei 5-61247 or JP Kokai Hei 2-190383.

The compounds and photoinitiator systems of the invention can be used still further in image recording materials as described, for example, in U.S. Pat. Nos. 4,842,980, 4,865,942 or 4,532,200. They can also be employed in microcapsule systems with latent dyes, as depicted, for example, in JP Kokai Hei 4255848 or JP Kokai Hei 5-318909, or in multicolour systems, as indicated, for example, in JP Kokai Hei 2-190386, JP Kokai Hei 2-190385, JP Kokai Hei 2-44 or JP Kokai Hei 2-223446.

The photosensitivity of the compositions of the invention extends in general from about 200 nm through the UV region into the infrared region (about 20 000 nm, in particular 1200 nm) and therefore spans a very broad range. Suitable radiation is present, for example, in sunlight or light from artificial light sources. Consequently, a large number of very different types of light source are employed. Both point sources and arrays ("lamp carpets") are suitable. Examples are carbon arc lamps, xenon arc lamps, medium-, high- and low-pressure mercury lamps, possibly doped with metal halides (metal-halogen lamps), microwave-excited metal vapour lamps, excimer lamps, superactinic fluorescent tubes, fluorescent lamps, argon incandescent lamps, electronic flashlamps, photographic floodlamps, light-emitting diodes (LEDs), electron beams and X-rays, produced by means of synchrotrons or laser plasma. The distance between the lamp and the substrate to be exposed in accordance with the invention may vary depending on the intended application and the type and output of the lamp, and may be, for example, from 2 cm to 150 cm. Laser light sources, for example excimer lasers, are especially suitable. Lasers in the visible region or in the IR region can also be employed. In this case, the high sensitivity of the materials of the invention and the possibility of adapting the dye to the laser line are very advantageous. By this method it is possible to produce printed circuits in the electronics industry, lithographic offset printing plates or relief printing plates, and also photographic and holographic image-recording materials and storage media.

The invention also provides a process for the photopolymerization of non-volatile monomeric, oligomeric or polymeric compounds containing at least one ethylenically unsaturated double bond, which comprises adding at least one photoinitiator as described above to said compounds and curing the mixture with electromagnetic radiation, especially light having a wavelength ranging from 200 nm up to and including the infrared region. The invention additionally provides a process as described above for preparing pigmented and unpigmented paints and varnishes, powder coatings, printing inks, printing plates, adhesives, dental compositions, optical waveguides, optical switches, colour-proofing systems, glass fibre cable coatings, screen printing stencils, resist materials, composite compositions, decolouring systems, including decolouring systems for image recording materials, for image recording materials using microcapsules, for encapsulating electrical and electronic components, for producing magnetic recording materials, for producing three-dimensional objects by stereolithography, for photographic reproductions, and for producing image recording material, especially for holographic recordings.

The invention also provides for the use of the above-described composition for preparing pigmented and unpigmented paints and varnishes, powder coatings, printing inks, printing plates, adhesives, dental compositions, optical waveguides, optical switches, colour-proofing systems, glass fibre cable coatings, screen printing stencils, resist materials, composite compositions, decolouring systems, including decolouring systems for image recording materials, for image recording materials using microcapsules, for encapsulating electrical and electronic components, for producing magnetic recording materials, for producing three-dimensional objects by stereolithography, for photographic reproductions, and image recording material, especially halographic recordings.

The invention additionally provides a coated substrate which is coated on at least one surface with a composition as described above, and a process for the photographic production of relief images, in which a coated substrate is subjected to imagewise exposure and then the unexposed portions are removed with a solvent. Imagewise exposure means either a) exposure through a mask or b) exposure by means of a movable laser beam. Of particular interest in this context is the laser beam exposure already mentioned above.

The polyborate compounds of the invention are reactive and in particular are also highly suitable as coinitiators in acidic formulations, since they exhibit good stability to acid.

The examples which follow illustrate the invention in more detail. Parts and percentages are, as in the remainder of the description and in the claims, by weight, unless stated otherwise.

EXAMPLE 1

Procedure for Preparing Bisborates from Alkylenebis[(dialkoxy)boranes]

Bis(tetramethylammonium) 1,6-hexylenebis[tris(m-fluorophenyl)]borate

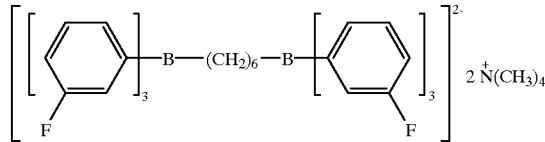

A small part of 7.0 g (0.04 mol) of 1-bromo-3-fluorobenzene is added to a suspension of 0.97 g (0.04 mol) of magnesium turnings in 20 ml of tetrahydrofuran (THF). The reaction mixture is heated until the Grignard reaction sets in. When reaction begins, heating is discontinued and the remainder of the 1-bromo-3-fluorobenzene is added dropwise over 20 minutes in such a way that gentle reflux is maintained. Following this addition, heating is continued until the rest of the magnesium has been consumed. After the Grignard solution has been cooled to room temperature, 1.38 g (0.006 mol) of 1,6-bis(dimethoxyboryl)hexane are added dropwise. After the end of this addition, the reaction mixture is heated at reflux for 2 hours. Subsequently, the mixture is concentrated in vacuo and the residue is treated with 40 ml of saturated sodium chloride salt solution. The resulting emulsion is extracted with ethyl acetate, and the organic phases are dried over magnesium sulfate, filtered and concentrated. The oily residue which results is dissolved in 80 ml of a 1:1 mixture of methanol and water. Following filtration and treatment of the filtrate with 1.4 g (0.013 mol) of tetramethylammonium chloride a white solid is precipitated. This solid is filtered off, treated with boiling methanol and dried in vacuo, giving 2.2 g of the borate of the invention with a melting point >230° C. The shift value δ in the $^{11}$B-NMR spectrum in $CD_3COCD_3$ is −4.95 ppm.

EXAMPLE 2

Bis(tetrabutylammonium)-1,6-hexylene-bis (triphenyl)borate

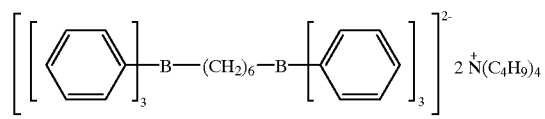

The compound is obtained by the method described in Example 1, using tetrabutylammonium bromide instead of tetramethylammonium chloride and 1-brombenzene instead of 1-bromo-3-fluorobenzene. In addition, the treatment with boiling methanol is omitted. The title product, with a melting point >230° C., is obtained in a yield of 44%. The shift values δ in the $^1$H-NMR spectrum, measured in acetone-$d_6$, are: 7.21 ppm (m,12); 6.74 ppm (br t, 12, J=6 Hz); 6.55 ppm (br t, 6 J=6 Hz); 3.27–3.20 ppm (br m, 16); 1.75–1.60 ppm (br m, 16); 1.32–1.20 ppm (br m, 16); 1.20–0.80 ppm (br m, 12) and 0.84 ppm (t, 24, J=7 Hz).

EXAMPLES 3–7

The compounds of Examples 3–7 are prepared by a method similar to that described in Example 1 but replacing tetramethylammonium chloride in each case by the onium chloride of the respective cation. The compounds are listed in Table 1 below.

TABLE 1

| Example | $Z^+$ | Melting range [° C.] |
|---|---|---|
| 3 | $N(C_{16}H_{33})(CH_3)_3$ | 103–106 |
| 4 | $N(C_2H_5)_3(benzyl)$ | 142–170 |
| 5 | $N(C_{10}H_{21})_2(CH_3)_2$ | Oil |
| 6 | $N(C_4H_9)_4$ | 120–126 |
| 7 | $P(C_4H_9)_4$ | >200 |

EXAMPLES 8–20

Examples 8 to 20 are prepared by the general method set out below using the respective diolefins, trisolefins and oniom chlorides. The compounds and their physical data are set out in Table 2.

Stage 1: Bis- or tris(dibromoborane-dimethyl sulfides)

0.5 equivalent of a diolefin or 0.33 equivalent of a triolefin is added dropwise at room temperature to a 1M solution of $HBBr_2—S(CH_3)_2$ in methylene chloride. The reaction mixture is heated at reflux until the olefin absorbances in the $^1$H-NMR spectrum have disappeared (about 5–24 h). Concentration of the methylene chloride gives a viscous resin consisting of an isomer mixture (cis and trans isomers and also regioisomers) of bis- or tris(dibromoboranes) in the form of their dimethyl sulfide complexes.

Stage 2: Bis- and tris(triarylalkyleneborates)

The bis- or tris(dibromoborane-dimethyl sulfides) described above are converted to the corresponding bis- and trisborates by the method described in GB 2 307 473 (Example 2). In this method, a small part of a solution of the respective aryl bromide in THF is added to a suspension of magnesium turnings in tetrahydrofuran (THF). The reaction mixture is heated until the Grignard reaction sets in. When the reaction begins, heating is discontinued and the remainder of the aryl bromide solution is added dropwise over 20 minutes in such a way that gentle reflux is maintained. Following the addition, heating is continued until the remainder of the magnesium has been consumed. In a different reaction vessel, THF is added slowly to the respective bis- or tris(dibromoborane-dimethyl sulfide), which has been cooled to 0° C. Then the Grignard solution is added dropwise over 30 minutes at the same temperature and, when addition is complete, the mixture is heated under reflux for 2 hours. Subsequently, the mixture is concentrated in vacuo and the oily residue which results is dissolved in a 4:1 mixture of methanol and water. Following filtration and treatment of the filtrate with the respective onium chloride, the respective compound of the invention is precipitated. The solid is filtered off, washed with water and dried in vacuo. Like the starting materials, the resulting borates are isomer mixtures. Table 2 below shows the compounds (in each case only one of the isomers obtained) and the physical data. For the $^{11}$B NMR data (measured in acetone-$d_6$), only the main signals ($\delta$) are given in each case.

TABLE 2

$[(Aryl)_3\text{-B--X--B-}(Aryl)_3]^{2-} \, 2Z^+$

| Ex. | Aryl | X | $Z^+$ | Melting range [° C.] | $^{11}$B-NMR $\delta$ [ppm] |
|---|---|---|---|---|---|
| 8*1 | 3-fluoro-phenyl | norbornane-diyl | $N(CH_3)_4$ | >200 | −2.99 |
| 9*1 | 4-chloro-phenyl | norbornane-diyl | $N(CH_3)_4$ | 180–210 | −3.63 |
| 10*2 | 4-methoxy-phenyl | 1,4-cyclooctylene | $N(CH_3)_4$ | 173–205 | −2.55 |
| 11*2 | 3-fluoro-phenyl | 1,4-cyclooctylene | $N(CH_3)_4$ | >200 | −1.62 |
| 12*2 | phenyl | 1,4-cyclooctylene | $N(C_4H_9)_4$ | 72–95 | −1.38 |
| 13*2 | phenyl | 1,4-cyclooctylene | $N(C_4H_9)_4$ | 48–77 | −1.38 |
| 14*2 | phenyl | 1,4-cyclooctylene | PhC(O)CH$_2$–S(CH$_3$)$_2$ | 84–98 | −1.38 |

TABLE 2-continued

[(Aryl)$_3$-B—X—B-(Aryl)$_3$]$^{2-}$ 2Z$^+$

| Ex. | Aryl | X | Z$^+$ | Melting range [° C.] | $^{11}$B-NMR δ [ppm] |
|---|---|---|---|---|---|
| 15*[3] | 3-fluoro-phenyl | —C$_2$H$_4$—C$_6$H$_4$—C$_2$H$_4$— | N(CH$_3$)$_4$ | 122–131 | −4.80 |
| 16*[3] | 3-methyl-phenyl | —C$_2$H$_4$—C$_6$H$_4$—C$_2$H$_4$— | N(CH$_3$)$_4$ | 113–121 | −5.00 |
| 17*[4] | 3-fluoro-phenyl | (cyclohexyl with CH$_3$ groups and —CH$_2$—CH(CH$_3$)— linker) | N(CH$_3$)$_4$ | 115–140 | −4.74 −2.44 |
| 18*[5] | phenyl | (cyclohexyl with —C$_2$H$_4$—B(phenyl)$_3$$^-$ N(CH$_3$)$_3$$^+$ substituent and —C$_2$H$_4$— linkers) | N(CH$_3$)$_4$ | >200 | −4.97 |
| 19*[5] | 3-fluoro-phenyl | (cyclohexyl with —(CH$_2$)$_2$—B[C$_6$H$_4$F]$_3$$^-$ $^+$N(CH$_3$)$_4$ substituent and —C$_2$H$_4$— linkers) | N(CH$_3$)$_4$ | 120–165 | −4.82 |
| 20*[6] | 3-fluoro-phenyl | (tricyclic norbornane-type structure) | N(CH$_3$)$_4$ | >200 | −2.78 |

*[1]Isomers: 2,5, 2,6 and endo and exo
*[2]Isomers: 1,4, 1,5 and cis and trans
*[3]Isomers: mixtures of 1-phenethyl and 2-phenethyl radicals
*[4]Isomers: mixtures of cis and trans
*[5]Isomers: mixtures of 1-cyclohexylethyl and 2-cyclohexylethyl radicals, and also cis and trans
*[6]Isomers: 3,8, 3,9, 4,8 and endo and exo In the following examples, use is made of the coinitiators shown below:

A

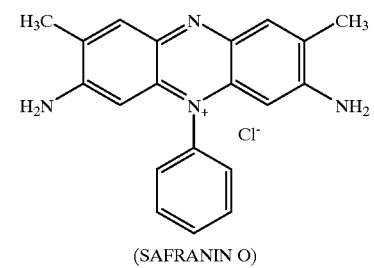

(SAFRANIN O)

B

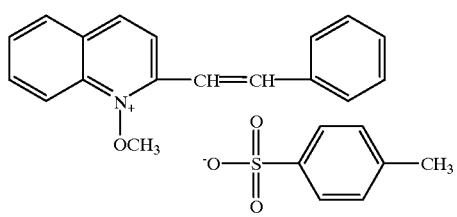

C

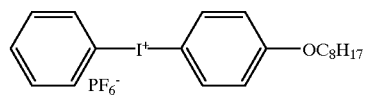

D

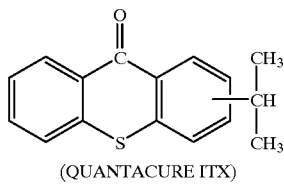

(QUANTACURE ITX)

E

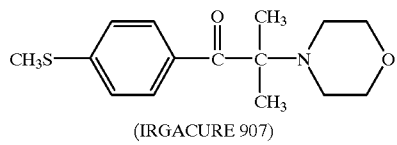

(IRGACURE 907)

F

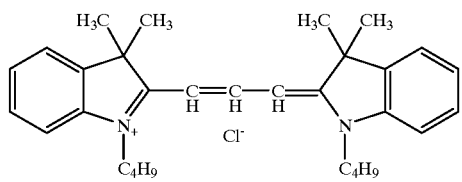

G

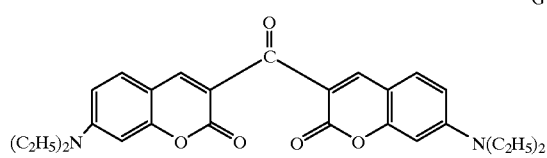

-continued

H

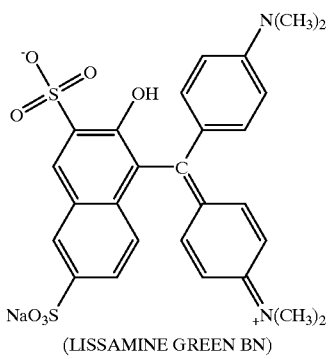

(LISSAMINE GREEN BN)

EXAMPLE 21

Reactivity Test in a Clearcoat

A photocurable composition is prepared by mixing the following components:

| | |
|---|---|
| 10.0 g | of dipentaerythritol monohydroxypentaacrylate (® SR399, Sartomer Co.) |
| 15.0 g | of tripropylene glycol diacrylate (Sartomer Co.) |
| 15.0 g | of N-vinylpyrrolidone (Fluka) |
| 10.0 g | of trimethylolpropane triacrylate (Degussa) |
| 50.0 g | of urethane acrylate (® Actylan AJ 20, Société Nationale des Poudres et Explosifs) |
| 0.3 g | of levelling assistant (® Byk 300, Byk-Mallinckrodt) |

Portions of this composition are mixed with 0.4%, based on the overall amount, of the borate compound of the invention and with 0.3% of a coinitiator. All operations are performed under red light. The samples to which the initiator has been added are applied to a 200 $\mu$m aluminium foil. The thickness of the dry layer is about 60 $\mu$m. To this film there is applied a 76 $\mu$m thick polyester film, over which a standardized test negative having 21 steps of different optical density (Stouffer wedge) is placed. The sample is covered with a second UV-transparent film and is pressed on a metal plate by means of vacuum. Exposure is carried out in a first test series for 5 seconds, in a second series for 10 seconds and in a third series for 20 seconds, using an MO61/5kW lamp at a distance of 30 cm. Following exposure, the films and the mask are removed and the exposed layer is developed in ethanol for 10 seconds at 23° C. in an ultrasound bath. Drying is carried out at 40° C. in a convection oven for 5 minutes. The sensitivity of the initiator system used is characterized by indicating the last wedge step which was reproduced without tack. The higher the number of steps, the more sensitive the system test. The results are summarized in Table 3.

TABLE 3

| Compound from Example | Coinitiator | Number of cured steps after | | |
|---|---|---|---|---|
| | | 5 s | 10 s | 20 s |
| 2 | A | 6 | 9 | 11 |
| 1 | B | 7 | 10 | 12 |

EXAMPLE 22

Further compounds of the invention are tested in the clearcoat in the formulation described in Example 21 and by the method described therein. The results, the compounds of the invention used and the coinitiators used, and also their quantity, are set out in Table 4 below.

TABLE 4

| Compound from Example | Coinitiator | Number of cured steps after | | |
|---|---|---|---|---|
| | | 5 s | 10 s | 20 s |
| 20 (0.4%) | A (0.3%) | 8 | 10 | 12 |
| 11 (0.4%) | A (0.3%) | 8 | 10 | 12 |
| 11 (0.4%) | A (0.3%) C (0.3%) | 11 | 13 | 15 |
| 11 (0.4%) | D (0.3%) E (2.0%) | 11 | 13 | 15 |

EXAMPLE 23

Photocuring of an Acrylate Mixture

A photocurable composition is prepared by mixing the following components:

| | | Solids content |
|---|---|---|
| 150.30 g | of ® Scripset 540 (30% strength solution of polystyrene-maleic anhydride copolymer in acetone); Monsanto | 45.1 g |
| 48.30 g | of trimethylolpropane triacrylate | 48.3 g |
| 6.60 g | of polyethylene glycol diacrylate | 6.6 g |
| | | 100.0 g |

Portions of this composition are mixed with in each case 0.4% of the borate compound of the invention from Example 1 and 0.3% o-chlorohexaarylbisimidazole*, based on the solids content of the composition. All operations are peformed under red light. The samples to which initiator has been added are applied in a thickness of 150 µm to 300 µm aluminium foil. The solvent is removed in a convection oven by heating at 60° C. for 15 minutes. Over the liquid layer there is placed a 76 µm thick polyester film, and, atop this film, a standardized test negative with 21 steps of different optical density (Stouffer wedge). Over this wedge a second polyester film is applied and the resulting laminate is fixed on a metal plate. The sample is then exposed using an MO61/5kW lamp at a distance of 30 cm, for 10 seconds in a first test series, 20 seconds in a second test series and 40 seconds in a third test series. Following exposure, the films and the mask are removed and the exposed layer is developed with a 0.85% strength aqueous solution of sodium carbonate for 120 seconds in an ultrasound bath and then is dried in a convection oven at 60° C. for 15 minutes. The sensitivity of the initiator system used is characterized by indicating the last wedge step which was reproduced without tack. The higher the number of steps, the more sensitive the system. The results are indicated in Table 5.

TABLE 5

| Compound from Example | Coinitiator | Number of cured steps after | | |
|---|---|---|---|---|
| | | 10 s | 20 s | 40 s |
| 1 | * | 3 | 6 | 9 |

*o-chlorohexaarylbisimidazole

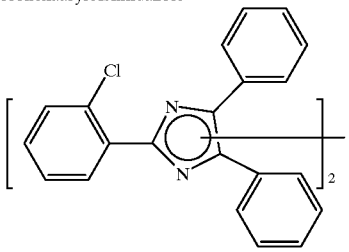

EXAMPLE 24

A formulation is prepared in the same way as for Example 23. The tests are also carried out as described in Example 23. The compounds tested, the coinitiators used and the results are set out in Table 6.

TABLE 6

| Compound from Example | Coinitiator | Number of cured steps after | | |
|---|---|---|---|---|
| | | 10 s | 20 s | 40 s |
| 15 | A | 10 | 13 | 15 |
| 19 | A | 9 | 12 | 14 |
| 17 | A | 11 | 13 | 15 |

EXAMPLE 25

Photocuring of a Monomer/polymer Mixture
(Reactivity Test in a Solder Resist)

A photocurable composition is prepared by mixing the following components:

| 37.64 g | of pentaerythritol triacrylate, (® Sartomer SR 444, Sartomer Company, Westchester) |
|---|---|
| 10.76 g | of hexamethoxymethylmelamine (® Cymel 301, American Cyanamid, USA) |
| 47.30 g | of thermoplastic polyacrylate with carboxyl groups (® Carboset 525, B. F. Goodrich) |
| 4.30 g | of polyvinylpyrrolidone PVP (GAF, USA) |

100.00 g of this composition are mixed with
319.00 g of methylene chloride and
30.00 g of methanol.

Portions of this composition are mixed with in each case 0.4% of the borate compound of the invention and 0.3% of a coinitiator, based on the solids content of the composition. All operations are performed under red light. The samples to which initiator has been added are applied to 300 µm aluminium plates using a 200 µm spiral-wound doctor blade. The dry layer thickness is about 35 µm. The solvent is removed in a convection oven by heating at 60° C. for 15 minutes. Over the liquid layer there is placed a 76 µm thick polyester film and, atop this film, a standardized test negative with 21 steps of different optical density (Stouffer wedge) is applied. The sample is covered with a second UV-transparent film and is pressed on a metal plate by means of vacuum. The sample is then exposed using an MO61/5kW lamp at a distance of 30 cm, for 10 seconds in a first test series, 20 seconds in a second test series and 40 seconds in a third test series. Following exposure, the films and the mask are removed, the exposed layer is developed with 0.85% strength aqueous sodium carbonate solution in a spray developer for 240 seconds, and then dried in a convection oven at 60° C. for 15 minutes. The sensitivity of the initiator system used is characterized by indicating the last wedge step reproduced without tack. The higher the number of steps, the more sensitive the system. The results are given in Table 7.

TABLE 7

| Compound from Example | Coinitiator | Number of cured steps after | | |
|---|---|---|---|---|
| | | 10 s | 20 s | 40 s |
| 2 | A | 10 | 12 | 14 |
| 1 | A | 9 | 11 | 13 |
| 1 | B | 7 | 9 | 11 |

EXAMPLE 26

A formulation is prepared as in Example 25. The tests are also carried out as described in Example 25. The compounds tested, the coinitiators used and the results are set out in Table 8.

TABLE 8

| Compound from Example | Coinitiator | Number of cured steps after | | |
|---|---|---|---|---|
| | | 10 s | 20 s | 40 s |
| 11 | F | 10 | 12 | 14 |
| 11 | G | 9 | 11 | 13 |
| 11 | H | 8 | 10 | 12 |
| 16 | G | 11 | 13 | 15 |
| 16 | F | 9 | 11 | 13 |
| 16 | H | 9 | 11 | 13 |

What is claimed is:
1. A compound of formula I or II

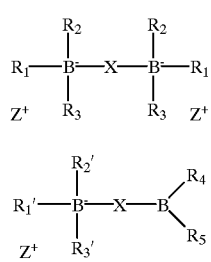

in which
R$_1$, R$_2$ and R$_3$ independently of one another are phenyl or another aromatic radical, which radicals are unsubstituted or substituted by C$_1$–C$_6$alkyl, halo-substituted-C$_1$–C$_6$alkyl, OR$_6$-substituted-C$_1$–C$_6$ alkyl, NR$_8$R$_9$-substituted-C$_1$–C$_6$alkyl, OR$_6$, S(O)$_p$R$_7$, OS(O)$_2$R$_7$, NR$_8$R$_9$, S(O)$_p$NR$_8$R$_9$, C(O)NR$_8$R$_9$, SiR$_{11}$R$_{12}$R$_{13}$, P(O)$_q$ R$_{14}$R$_{15}$, halo or

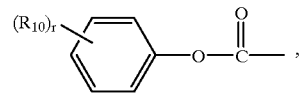

and none of the radicals R$_1$–R$_3$ is a phenyl radical substituted ortho to the bond to the borate atom or another aromatic radical substituted ortho to the borate atom;
p is 0, 1 or 2;
q is 0 or 1;
r is a number from 0 to 5;
R$_1$', R$_2$' and R$_3$' have one of the meanings of R$_1$–R$_3$ where the radicals R$_1$', R$_2$' and R$_3$' can also be substituted ortho to the bond to the borate atom;
R$_4$ and R$_5$ are OH or OR$_6$ or have one of the meanings of R$_1$–R$_3$ where the radicals R$_4$ and R$_5$ can also be substituted ortho to the bond to the borate atom;
R$_6$ and R$_7$ independently of one another are C$_3$–C$_{12}$cycloalkyl, C$_2$–C$_8$alkenyl, C$_1$–C$_{12}$alkyl, C$_1$–C$_{12}$alkoxy-substituted-C$_1$–C$_{12}$alkyl, halo-substituted-C$_1$–C$_{12}$alkyl, phenyl, mono- to penta-C$_1$–C$_6$alkyl-substituted-phenyl, C$_1$–C$_{12}$alkoxy-substituted-phenyl, halo-substituted-phenyl, phenyl-C$_1$–C$_6$alkyl, mono- to penta-C$_1$–C$_6$alkyl-substituted-phenyl-C$_1$–C$_6$alkyl, C$_1$–C$_{12}$alkoxy-substituted-phenyl-C$_1$–C$_6$alkyl or halo-substituted-phenyl-C$_1$–C$_6$-alkyl;
R$_8$, R$_9$, R$_{11}$, R$_{12}$, R$_{13}$, R$_{14}$ and R$_{15}$ independently of one another have one of the meanings of R$_6$, or R$_8$ and R$_9$, together with the nitrogen atom to which they are attached, form a 5- or 6-membered ring which may additionally contain oxygen or sulfur atoms;
R$_{10}$ is hydrogen or C$_1$–C$_{12}$alkyl;
X is C$_1$–C$_{20}$alkylene, which is unsubstituted or substituted by OR$_6$', S(O)$_p$R$_7$', OS(O)$_2$R$_7$', NR$_8$'R$_9$', C(O)NR$_8$'R$_9$', SiR$_{11}$'R$_{12}$'R$_{13}$', P(O)$_q$R$_{14}$'R$_{15}$', halo, (BR$_1$R$_2$R$_3$)$^-$Z$^+$, BR$_4$R$_5$, phenyl or

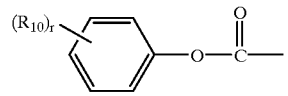

where the phenyl radical is unsubstituted or substituted 1 to 5 times by halo, C$_1$–C$_{12}$alkyl, (BR$_1$R$_2$R$_3$)$^-$Z$^+$-substituted-C$_1$–C$_{12}$alkyl, BR$_4$R$_5$-substituted-C$_1$–C$_{12}$alkyl, C$_1$–C$_{12}$dialkylamino, (BR$_1$R$_2$R$_3$)$^-$Z$^+$-substituted-C$_1$–C$_{12}$dialkylamino, BR$_4$R$_5$-substituted-C$_1$–C$_{12}$dialkylamino, C$_1$–C$_{12}$alkoxy, (BR$_1$R$_2$R$_3$)$^-$Z$^+$-substituted-C$_1$–C$_{12}$alkoxy or BR$_4$R$_5$-substituted-C$_1$–C$_{12}$alkoxy; or
X is C$_2$–C$_{20}$alkylene which is interrupted by one or more groups -O-, -S(O)$_p$-, -NR$_{16}$-, -OSiR$_{17}$R$_{18}$O- or -SiR$_{17}$R$_{18}$-; or
X is C$_2$–C$_{20}$alkylene which is interrupted by one or more aromatic radical where the aromatic radicals are unsubstituted or substituted 1 to 5 times by halo, (BR$_1$R$_2$R$_3$)$^-$Z$^+$, BR$_4$R$_5$, C$_1$–C$_6$alkyl, (BR$_1$R$_2$R$_3$)$^-$Z$^+$-substituted-C$_1$–C$_6$alkyl, BR$_4$R$_5$-substituted-C$_1$–C$_6$alkyl, C$_1$–C$_{12}$alkoxy, (BR$_1$R$_2$R$_3$)$^-$Z$^+$-substituted-C$_1$–C$_{12}$alkoxy, BR$_4$R$_5$-substituted-C$_1$–C$_{12}$alkoxy, C$_1$–C$_{12}$dialkylamino, (BR$_1$R$_2$R$_3$)$^-$Z$^+$-substituted-C$_1$–C$_{12}$dialkylamino or BR$_4$R$_5$-substituted-C$_1$–C$_{12}$dialkylamino; or X is $C_3$–$C_{12}$cycloalkylene or $C_2$–$C_8$alkenylene which is unsubstituted or substituted by $OR_6'$, $S(O)_pR_7'$, $OS(O)_2R_7'$, $NR_8'R_9'$, $C(O)NR_8'R_9'$, $SiR_{11}'R_{12}'R_{13}'$, $P(O)_qR_{14}'R_{15}'$, halo, $C_1$–$C_{12}$alkyl, $(BR_1R_2R_3)^-Z^+$, $BR_4R_5$, phenyl or

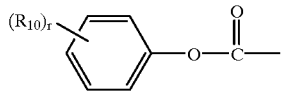

where the phenyl radical is unsubstituted or substituted 1 to 5 times by halo, $C_1$–$C_{12}$alkyl, $(BR_1R_2R_3)^-Z^+$-substituted-$C_1$–$C_{12}$alkyl, $BR_4R_5$-substituted-$C_1$–$C_{12}$alkyl, $C_1$–$C_{12}$dialkylamino, $(BR_1R_2R_3)^-Z^+$-substituted-$C_1$–$C_{12}$dialkylamino, $BR_4R_5$-substituted-$C_1$–$C_{12}$dialkylamino, $C_1$–$C_{12}$alkoxy, $(BR_1R_2R_3)^-Z^+$-substituted-$C_1$–$C_{12}$alkoxy or $BR_4R_5$-substituted-$C_1$–$C_{12}$alkoxy; or X is $C_3$–$C_{12}$cycloalkylene or $C_2$–$C_8$alkenylene which is interrupted by one or more groups -O-, -S(O)$_p$-, -NR$_{16}$-, -OSiR$_{17}$R$_{18}$O- or -SiR$_{17}$R$_{18}$-; or X is a radical of formula X–XVII

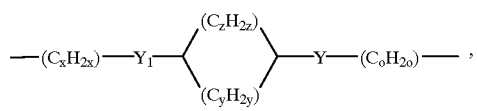
(X)

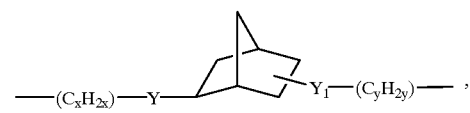
(XI)

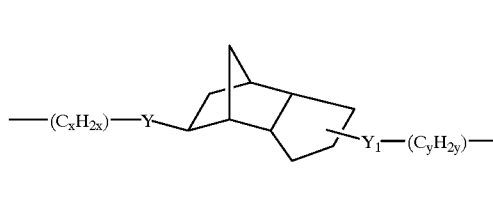
(XII)

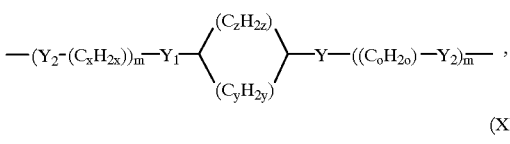
(XIII)

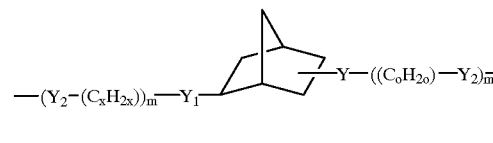
(XIV)

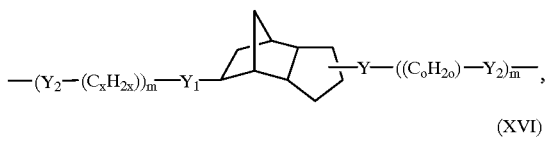
(XV)

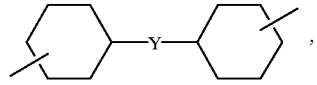
(XVI)

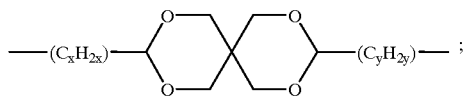
(XVII)

or X is polycycloalkylene;

x, y, z and o independently of one another are a number from 0 to 8, where the cycloalkyl rings in the formulas (X) and (XIII) in each case contain not more than 12 carbon atoms;

m is a number from 1 to 6;

$R_6'$ and $R_7'$ independently of one another are $C_1$–$C_{12}$alkyl which is unsubstituted or substituted by $C_1$–$C_{12}$alkoxy, $(BR_1R_2R_3)^-Z^+$-substituted-$C_1$–$C_{12}$alkoxy, $BR_4R_5$-substituted-$C_1$–$C_{12}$alkoxy, $C_1$–$C_{12}$dialkylamino, $(BR_1R_2R_3)^-Z^+$-substituted-$C_1$–$C_{12}$dialkylamino, $BR_4R_5$-substituted-$C_1$–$C_{12}$dialkylamino, halo, $(BR_1R_2R_3)^-Z^+$ or $BR_4R_5$;

or $R_6'$ and $R_7'$ are $C_3$–$C_{12}$cycloalkyl which is unsubstituted or substituted by $C_1$–$C_{12}$alkoxy-substituted-$C_3$–$C_{12}$cycloalkyl, $C_1$–$C_{12}$dialkylamino-substituted-$C_3$–$C_{12}$cycloalkyl, halo-substituted-$C_3$–$C_{12}$cycloalkyl, $(BR_1R_2R_3)^-Z^+$-substituted-$C_3$–$C_{12}$cycloalkyl, $BR_4R_5$-substituted-$C_3$–$C_{12}$cycloalkyl, or $R_6'$ and $R_7'$ are phenyl, mono-to penta-halo-substituted phenyl, phenyl substituted by $C_1$–$C_6$alkyl, $(BR_1R_2R_3)^-Z^+$-substituted-$C_1$–$C_6$alkyl, $BR_4R_5$-substituted-$C_1$–$C_6$alkyl, $C_1$–$C_{12}$alkoxy, $(BR_1R_2R_3)^-Z^+$-substituted-$C_1$–$C_{12}$alkoxy, $BR_4R_5$-substituted-$C_1$–$C_{12}$alkoxy, $C_1$–$C_{12}$dialkylamino, $(BR_1R_2R_3)^-Z^+$-substituted-$C_1$–$C_{12}$dialkylamino or $BR_4R_5$-substituted-$C_1$–$C_{12}$dialkylamino; or $R_6'$ and $R_7'$ are phenyl-$C_1$–$C_6$alkyl, mono-to penta-halo-substituted phenyl-$C_1$–$C_6$alkyl, phenyl-$C_1$–$C_6$alkyl substituted by $C_1$–$C_6$alkyl, $(BR_1R_2R_3)^-Z^+$-substituted-$C_1$–$C_6$alkyl, $BR_4R_5$-substituted-$C_1$–$C_6$alkyl, $C_1$–$C_{12}$alkoxy, $(BR_1R_2R_3)^-Z^+$-substituted-$C_1$–$C_{12}$alkoxy, $BR_4R_5$-substituted-$C_1$–$C_{12}$alkoxy, $C_1$–$C_{12}$dialkylamino, $(BR_1R_2R_3)^-Z^+$-substituted-$C_1$–$C_{12}$dialkylamino or $BR_4R_5$-substituted-$C_1$–$C_{12}$dialkylamino;

$R_8'$, $R_9'$, $R_{11}'$, $R_{12}'$, $R_{13}'$, $R_{14}'$ and $R_{15}'$ independently of one another have one of the meanings of $R_6'$, or $R_8'$ and $R_9'$, together with the nitrogen atom to which they are attached, form a 5- or 6-membered ring which may additionally contain oxygen or sulfur atoms;

$R_{16}$ is hydrogen or has one of the meanings of $R_6'$;

$R_{17}$ and $R_{18}$ have one of the meanings of $R_6'$;

Y, $Y_1$ and $Y_2$ independently of one another are a direct bond, O, S, $SO_2$, $NR_{16}$, $SiR_{17}R_{18}$ or —$CR_{19}R_{20}$;

$R_{19}$ and $R_{20}$ independently of one another are hydrogen or $C_1$–$C_{12}$alkyl; and $Z^+$ is a radical which is able to form a positive ion.

2. A compound of the formula I or II according to claim 1, in which $R_1$, $R_2$ and $R_3$ independently of one another are unsubstituted phenyl or phenyl which is substituted by $C_1$–$C_6$alkyl, halo-substituted $C_1$–$C_6$alkyl, $OR_6$, $S(O)_p$ $NR_8R_9$ or $C(O)NR_8R_9$;

$R_1'$, $R_2'$, $R_3'$, $R_4$ and $R_5$ have one of the meanings of $R_1$–$R_3$, where the radicals $R_1'$, $R_2'$, $R_3'$, $R_4$ and $R_5$ can also be substituted ortho to the bond to the borate atom;

$R_6$, $R_7$, $R_8$ and $R_9$ are $C_1$–$C_{12}$alkyl or phenyl;

or $R_8$ and $R_9$, together with the nitrogen atom to which they are attached, form a 5- or 6-membered ring which may additionally contain oxygen atoms;

X is $C_2$–$C_{20}$alkylene or is $C_1$–$C_{20}$alkylene interrupted by one or more groups -O-, $SO_2$- or $NR_{16}$-, or X is an alkylene of the following formulae III–IX:

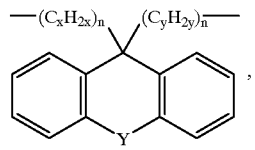  (III)

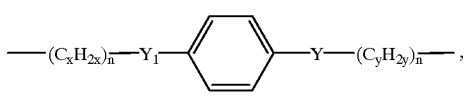  (IV)

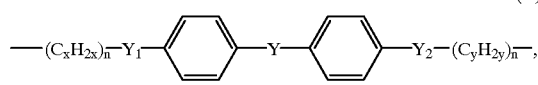  (V)

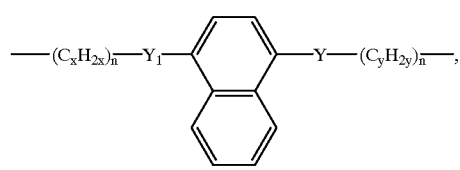  (VI)

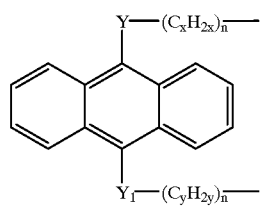  (VII)

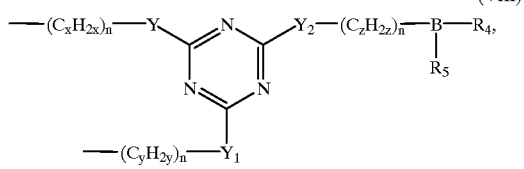  (VIII)

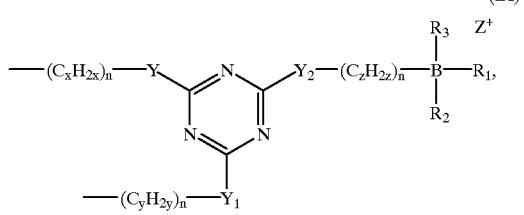  (IX)

in which n is a number from 1 to 6 and the phenyl rings may be substituted by $C_1$–$C_{12}$alkoxy, or X is $C_3$–$C_{12}$cycloalkylene which is unsubstituted or substituted by $(BR_1R_2R_3)^-Z^+$ or $C_1$–$C_{12}$alkyl, and Y, $Y_1$ and $Y_2$ independently of one another are a direct bond or O.

3. A compound according to claim 1, in which Z is a mono- or divalent dye cation or metal complex, sulfonium, sulfoxonium or iodonium cation, or Z is a UV absorber compound which is able to form cations, or Z is a metal cation of group I of the Periodic Table, or Z is a cation $MY_b^+$, where M is a metal of group II of the Periodic Table and $Y_b$ is alkoxy or halo, or Z is an ammonium salt or phosphonium salt.

4. A compound of the formula I according to claim 1, in which $R_1$, $R_2$ and $R_3$ are unsubstituted or halo-, $OR_6$- or $C_1$–$C_4$alkyl-substituted phenyl, $R_6$ is $C_1$–$C_4$alkyl, X is $C_2$–$C_6$alkylene, $C_2$–$C_6$alkylene interrupted by phenylene, or $C_6$–$C_{12}$cycloalkylene unsubstituted or substituted by $(BR_1R_2R_3)^-Z^+$, and Z is a tetraalkylammonium or sulfonium cation.

5. A photoinitiator comprising (A) at least one compound of the formula I or II according to claim 1 as coinitiator and (B) at least one electron acceptor compound, where the electron acceptor compound (B) can also be a constitutent of the radical $Z^+$ of the formula I.

6. A photoinitiator according to claim 5, in which the electron acceptor compound (B) is a dye or a UV absorber.

7. A photoinitiator according to claim 6, in which the UV absorber is a thioxanthone derivative, coumarin, benzophenone, a benzophenone derivative or a hexaarylbisimidazole derivative.

8. A photoinitiator according to claim 6, in which the dye is a cyanine dye or quinolinium dye.

9. A photoinitiator according to claim 6, in which the dye is a dye which loses or changes its color in the course of or after irradiation.

10. A photoinitiator according to claim 5, comprising in addition to the coinitiator (A) a further borate compound ($A_1$) as coinitiator.

11. A composition comprising
   (a) at least one ethylenically unsaturated photopolymerizable compound; and
   (b) at least one photoinitiator according to claim 5.

12. A composition according to claim 11, comprising in addition to component (b) a further photoinitiator (c) and/or other additives (d).

13. A composition according to claim 12, comprising as further photoinitiator (c) at least one titanocene, ferrocene, benzophenone, benzoin alkyl ether, benzil ketal, 4-aroyl-1, 3-dioxolane, dialkoxyacetophenone, $\alpha$-hydroxy- or $\alpha$-aminoacetophenone, $\alpha$-hydroxycycloalkyl phenyl ketone, phenylglyoxalic ester or derivatives thereof, xanthone, thioxanthone, anthraquinone, another borate or a mono-, bis- or trisacylphosphine oxide, or mixtures thereof.

14. A composition according to claim 13, comprising as further photoinitiator (c) at least one $\alpha$-amino ketone compound.

15. A composition according to claim 12, in which a readily reducible compound is used as further additive (d).

16. A composition according to claim 15, in which as readily reducible compound a halogenated hydrocarbon is used.

17. A composition according to claim 11, comprising in addition to components (a) and (b) at least one neutral, anionic or cationic dye or a thioxanthone compound and an onium compound.

18. A composition according to claim 17, comprising in addition a free-radical photoinitiator (c).

19. A composition according to claim 17 wherein the compound of component (c) is an $\alpha$-amino ketone compound.

20. A composition according to claim 11, comprising from 0.05 to 15% by weight of component (b), or of components (b)+(c), based on the composition.

21. A composition according to claim 20 wherein the weight of component (b) is from 0.2 to 5% by weight based on the composition.

22. A process for the photopolymerization of non-volatile monomeric, oligomeric or polymeric compounds containing at least one ethylenically unsaturated double bond, which comprises adding at least one photoinitiator according to claim 5 to the abovementioned compounds and curing the mixture with electromagnetic radiation.

23. A process according to claim 22 for preparing pigmented and unpigmented paints and varnishes, powder coatings, printing inks, printing plates, adhesives, dental compositions, optical waveguides, optical switches, colour-proofing systems, glass fibre cable coatings, screen printing stencils, resist materials, composite compositions, decoloring systems, for image recording materials using microcapsules, for encapsulating electrical and electronic components, for producing magnetic recording materials, for producing three-dimensional objects by stereolithography, for photographic reproductions, or for producing image recording material.

24. A process according to claim 22 for producing holographic recordings.

25. A coated substrate which is coated on at least one surface with a composition according to claim 11.

26. A process for the photographic production of relief images, which comprises subjecting a coated substrate according to claim 25 either a) to imagewise exposure through a mask or b) to exposure through by means of a movable laser beam (without a mask) and then removing the unexposed portions with a solvent.

* * * * *